US009351963B2

(12) United States Patent
De Leeuw et al.

(10) Patent No.: US 9,351,963 B2
(45) Date of Patent: May 31, 2016

(54) DEFENSIN-LIKE MOLECULES AS NOVEL ANTIMICROBIAL AGENTS

(71) Applicant: UNIVERSITY OF MARYLAND, BALTIMORE, Baltimore, MD (US)

(72) Inventors: Erik De Leeuw, Baltimore, MD (US); Alexander D. Mackerell, Jr., Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 387 days.

(21) Appl. No.: 13/911,234

(22) Filed: Jun. 6, 2013

(65) Prior Publication Data

US 2013/0331413 A1    Dec. 12, 2013

Related U.S. Application Data

(60) Provisional application No. 61/656,039, filed on Jun. 6, 2012, provisional application No. 61/410,112, filed on Nov. 4, 2010.

(51) Int. Cl.

| A61K 31/35 | (2006.01) |
|---|---|
| A61K 31/351 | (2006.01) |
| A61K 31/40 | (2006.01) |
| A61K 31/403 | (2006.01) |
| A61K 31/428 | (2006.01) |
| A61K 31/404 | (2006.01) |
| A61K 31/4174 | (2006.01) |
| A61K 31/09 | (2006.01) |
| A61K 31/05 | (2006.01) |
| A61K 31/4709 | (2006.01) |
| A61K 31/433 | (2006.01) |

(52) U.S. Cl.
CPC ............. *A61K 31/428* (2013.01); *A61K 31/05* (2013.01); *A61K 31/09* (2013.01); *A61K 31/35* (2013.01); *A61K 31/351* (2013.01); *A61K 31/40* (2013.01); *A61K 31/403* (2013.01); *A61K 31/404* (2013.01); *A61K 31/4174* (2013.01); *A61K 31/433* (2013.01); *A61K 31/4709* (2013.01)

(58) Field of Classification Search
CPC ..... A61K 31/35; A61K 31/351; A61K 31/40; A61K 31/403
See application file for complete search history.

(56) References Cited

U.S. PATENT DOCUMENTS

| 4,840,784 | A | 6/1989 | Frank |
|---|---|---|---|
| 6,399,370 | B1 | 6/2002 | Wilson et al. |
| 2003/0013836 | A1 | 1/2003 | Takanishi |
| 2003/0092685 | A1 | 5/2003 | Nitz |
| 2004/0137482 | A1 | 7/2004 | Eckert |

OTHER PUBLICATIONS

Wang et al. (Phys. Chem. Chem. Phys., 2004, 6, 3437-3446), May 17, 2004.
Garcia-Acosta et al. (Chem. Commun., 2006, 2239-2241), May 2, 2006.
Fighting the Impact of Antibiotic-Resistant Bacteria, FDA Consumer Health Information, 2013.
Reb Lai et al., "Two novel non-cationic defensin-like antimicrobial peptides from haemolymph of the female tick, Amblyomma hebraeum", Biochemical Journal, 2004, vol. 379, pp. 681-685, see p. 681.
International Search Report in related application PCT/US2011/059432.
Written Opinion in related application PCT/US2011/059432.
International Preliminary Report on Patentability in related application PCT/US2011/059432.
Rurack et al., Chemical Physics Letters, 2000, 320, 87-94.
See also co-pending related U.S. Appl. No. 13/883,564.

*Primary Examiner* — Yong Chong
(74) *Attorney, Agent, or Firm* — Kristina Castellano; Castellano PLLC

(57) ABSTRACT

Disclosed are compositions and methods for treating and/or preventing infections in mammals, by administering to a mammal a therapeutically effective amount of at least one defensin-like molecule, e.g., in a composition that includes such molecule. Also disclosed are kits that include such molecules, or compositions that include such molecules, as well as instructions for using such molecules to treat a mammal.

6 Claims, 29 Drawing Sheets

FIG. 1
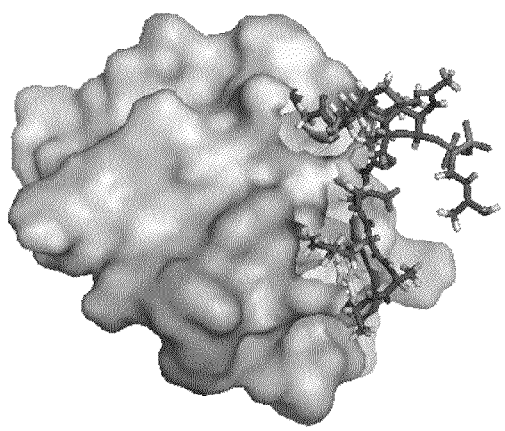
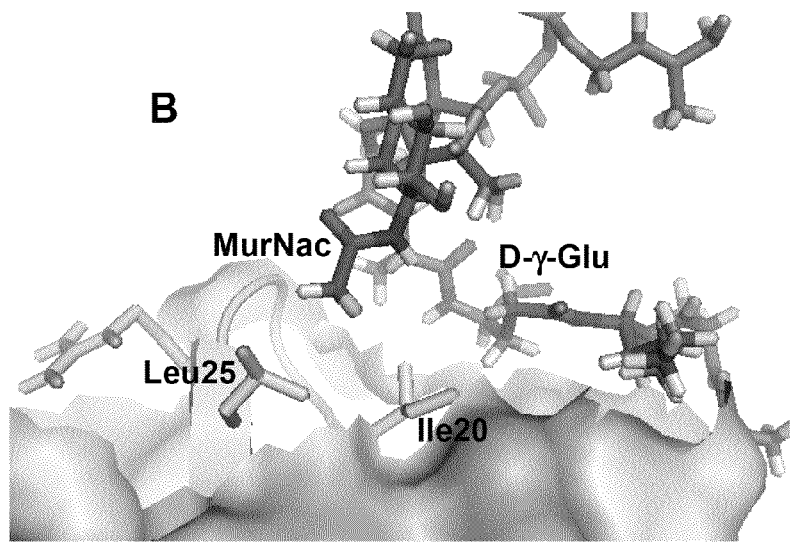
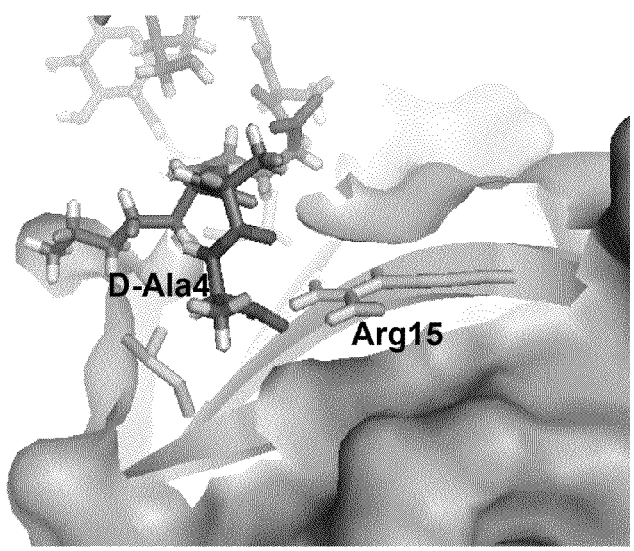

FIG. 4
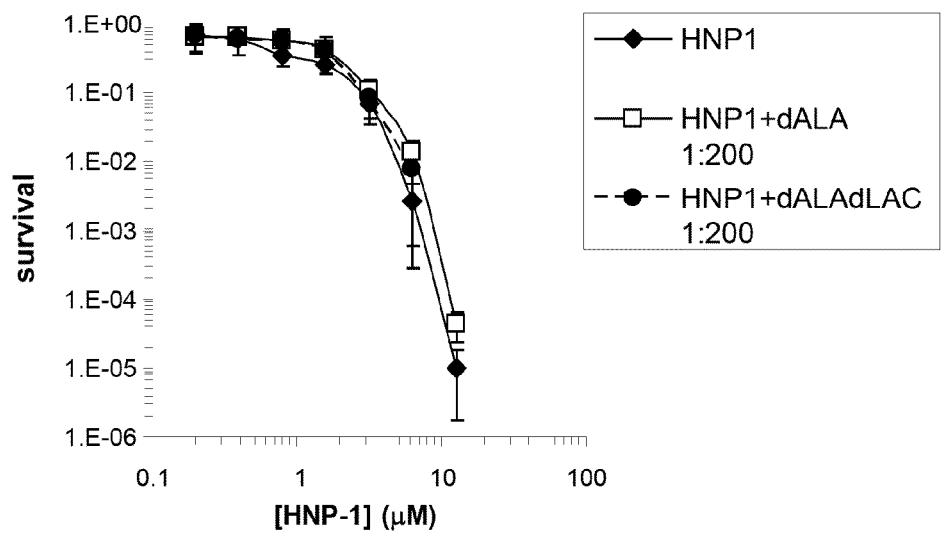
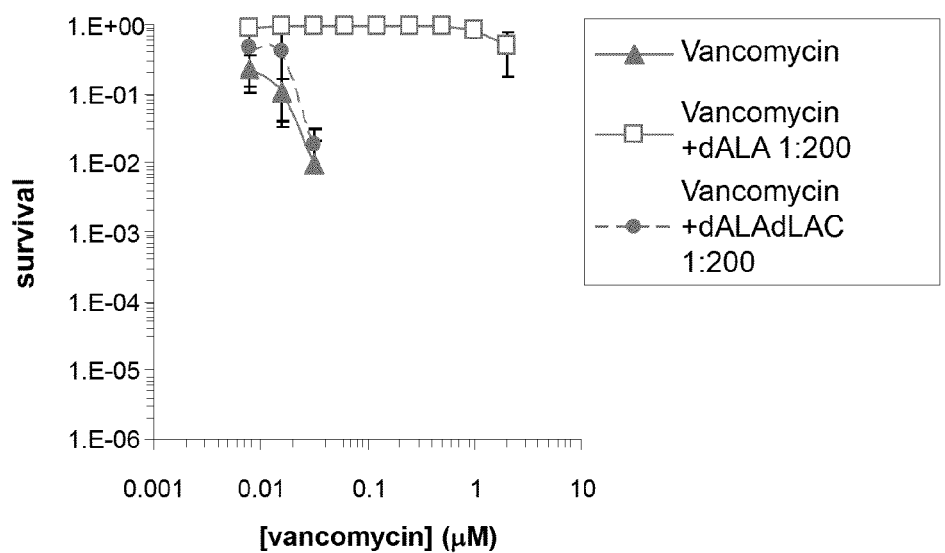

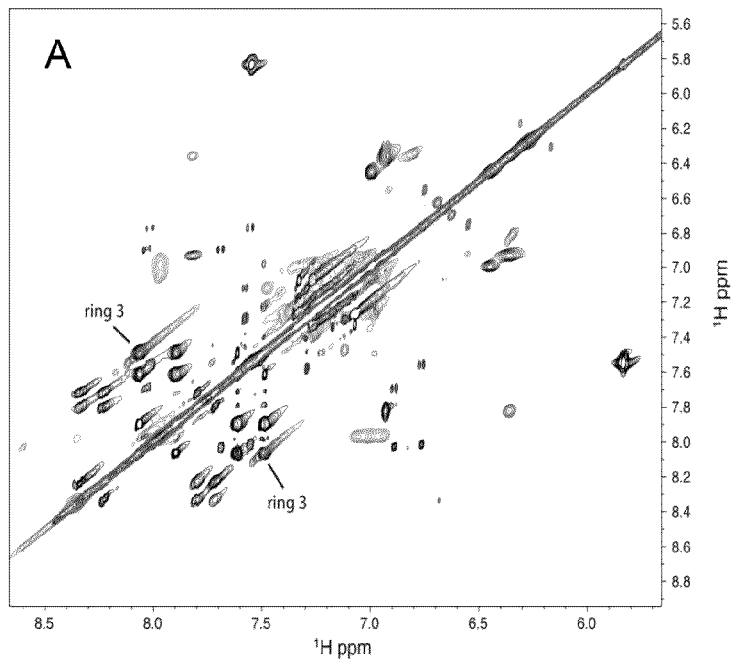
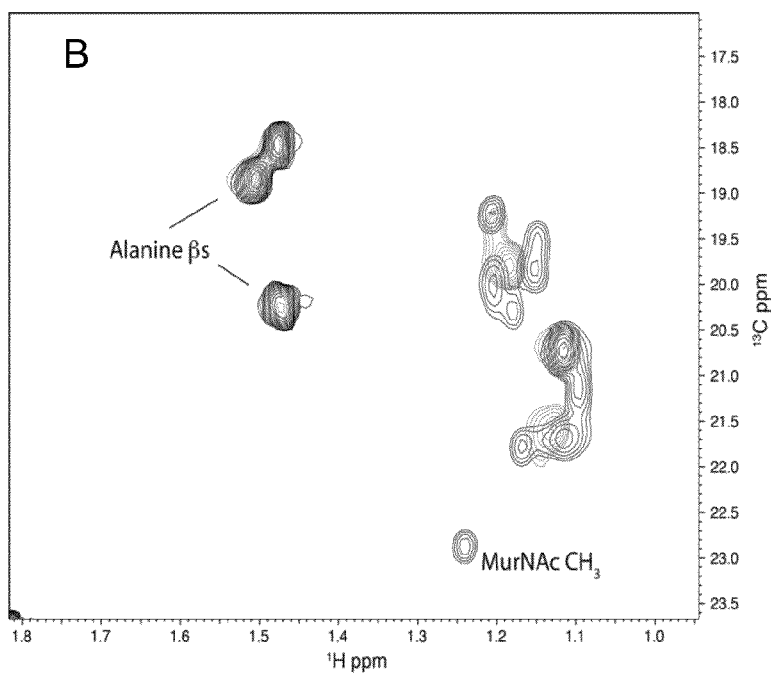
FIG. 7

FIG. 9

Table 1: Residues involved in HNP-1 Lipid II contacts. Common three letter abbreviation is used for amino acids. D: amino acid in D-configuration. MurNac: N-acetyl Muramic acid. The contact statistics is based on an analysis of the top 4 docking models.

| 3-Lipid II | HNP-1 | Nature of interaction |
|---|---|---|
| MurNac | Ile20, Arg24, Leu25 (monomer A), Leu25 (Monomer B) | Non-bonded (4) |
| Ala1 | Ile20, Gly23 (Monomer A) | Non-bonded (2) |
| Lys3 | Ile20 (Monomer A) | Non-bonded (1) |
| D-Ala4 | Arg15 (Monomer B) | Predicted Hydrogen bonding (1) |

FIG. 10

Table 2: Classification of lead defensin mimetics.

| Compound ID | Bacterial Killing (μM) | | Lipid II binding ($K_d$, μM) | Cytotoxicity ($C_{50\%}$, μM) | |
|---|---|---|---|---|---|
| | S. aureus | E. coli | | Caco-2 | Jurkat |
| Class I | | | | | |
| BAS00127538 | 0.244 | 7.8 | 1.71 | 2.7 | 14.5 |
| 1499-1221 | 0.031 | 125 | N.D. | 8.9 | 18.6 |
| 1493-0289 | 3.9 | 125 | 4.26 | 6.8 | 41.7 |
| Class II | | | | | |
| 5107930 | 23.4 | 125 | 3.64 | 27.9 | >223 |
| 4090-1978 | 15.6 | 62.5 | N.D. | 16.7 | 87.3 |
| Class III | | | | | |
| 363003 | 3.9 | >500 | 39.5 | 3.5 | 12.7 |
| 1611-0203 | 3.9 | >500 | 59.6 | 4.2 | 63.4 |

N.D: Not Determinable by SPR. Bacterial killing: Concentration resulting in 100% killing after exposure of compound to bacteria for 30 min, determined by modified vCC assays (25). Binding to immobilized 3-Lipid II was analyzed by Surface Plasmon Resonance. $C_{50\%}$ equals compound concentration resulting in 50% cell survival measured by MTT assay following incubation for 24 h (Caco-2) or 4 h (Jurkat).

FIG. 11

Table 3: Broth microdilution susceptibility testing for lead defensin mimetics and comparators. Experiments were carried out according to CLSI standards (26) by Micromyx, LLC (Kalamazoo, Michigan). MIC values for comparators (Ciprofloxin and Linezolid) were within QC range (54).

| | | MIC(µg/mL) | | | | | | | | |
|---|---|---|---|---|---|---|---|---|---|---|
| Organism: | MMX#-ATCC# | BAS00127538 | 1499-1221 | 1493-0289 | 5109730 | 4090-1978 | 363003 | 1611-0203 | Ciprofloxacin | Linezolid |
| Staphylococcus aureus | 100-29213 | 0.5 | 0.25 | 1 | 16 | 2 | 1 | 2 | 0.5 | 4 |
| Staphylococcus aureus (MRSA) | 757-NA | 0.5 | 0.5 | 2 | 16 | 2 | 1 | 2 | >2 | 4 |
| Enterococcus faecalis | 101-29212 | 1 | 2 | 2 | 16 | 16 | 1 | 1 | 1 | 2 |
| Enterococcus faecalis (VRE) | 848-NA | 1 | 2 | 4 | 16 | 16 | 1 | 1 | >2 | 2 |
| Streptococcus pneumoniae | 1195-49619 | 8 | >8 | 16 | >64 | >8 | 8 | >16 | 1 | 2 |
| Streptococcus pneumoniae (PRSP) | 884-NA | 8 | >8 | 16 | >64 | >8 | 16 | >16 | 2 | 2 |
| Escherichia coli | 102-25922 | 4 | >16 | >8 | >16 | 64 | >32 | >4 | 0.008 | >64 |
| Pseudomonas aeruginosa | 103-27853 | >8 | >16 | >8 | >16 | >64 | >32 | >4 | 0.25 | >64 |

Reported MICs were adjusted to reflect instances where drug precipitation obscured the interpretation of the endpoint NA-not applicable, MRSA-methicillin-resistant *S. aureus*, VRE-vancomycin-resistant enterococci, PRSP-penicillin-resistant *S. pneumoniae*

FIG. 13

MIC's (ug/ml)

| | Organism | Strain | BAS00127538 | 1499-1221 | 363003 | 7771-0701 | 4090-1978 | 1611-0203 | Ciprofloxacin |
|---|---|---|---|---|---|---|---|---|---|
| Bacillus | B. anthracis | Ames | 0.5 | 1 | 32 | >64 | 16 | 0.5 | 0.12 |
| Burkholderia | B. mallei | ATCC-23344 | >64 | >64 | >64 | >64 | >64 | >64 | 2 |
| Burkholderia | B. pseudomallei | K96243 | 64 | >64 | >64 | >64 | >64 | >64 | 2 |
| Yersinia | Y. pestis | CO92 | 8 | >64 | >64 | >64 | >64 | >64 | <0.06 |
| Francisella | F. tularensis | Schu4 | 2 | 1 | >64 | >64 | 32 | n/a | 1 |
| Bacillus | B. anthracis (spores) | Ames | 0.5 | 0.5 | 32 | >64 | 32 | 1 | 0.06 |

FIG. 14

| ID | structural formula | chemical formula | colored? | MW (g/mol) | IUPAC name | MFR | Binding on Lipid II? | active against S.aureus | active against E.coli | cytotoxic for Caco II (C$_{50\%}$ survival) | cytotoxic for Jurkat (C$_{50\%}$ survival) | compound category | Nr. |
|---|---|---|---|---|---|---|---|---|---|---|---|---|---|
| | | | | | | | | | | plate A | | | |
| 5457685 | | C$_{22}$H$_{28}$FN$_3$ | no | 353.5 | 1-(1-benzyl-4-piperidinyl)-4-(4-fluorophenyl)piperazine | Chem Bridge | No | No | No | No | ? | A | 1 |
| 5452876 | | C$_{16}$H$_{23}$F$_3$N$_2$ | no | 300.4 | 1-propyl-N-[3-(trifluoromethyl)benzyl]-4-piperidinamine | Chem Bridge | No | No | No | No | ? | A | 2 |
| 5270046 | | C$_{23}$H$_{23}$ClN$_2$ | no | 362.9 | 1-(4-biphenylylmethyl)-4-(4-chlorophenyl)piperazine | Chem Bridge | No | No | No | No | ? | A | 3 |
| 6711103 | | C$_{23}$H$_{30}$FN$_3$ | no | 367.5 | 1-(2-fluorophenyl)-4-[1-(4-methylbenzyl)-4-piperidinyl]piperazine | Chem Bridge | No | No | No | No | ? | A | 4 |
| 5418391 | | C$_{25}$H$_{23}$F$_3$N$_2$ | no | 408.5 | 1-(9H-fluoren-2-ylmethyl)-4-[3-(trifluoromethyl)phenyl]piperazine | Chem Bridge | No | No | No | Yes (159) | ? | A | 5 |

FIG. 14 (continued)

| ID | Structure | Formula | | MW | Name | Source | | | | | | | Plate B |
|---|---|---|---|---|---|---|---|---|---|---|---|---|---|
| 5267798 | 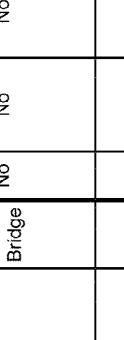 | $C_{23} H_{23} F N_2$ | no | 346.4 | 1-(4-biphenylylmethyl)-4-(4-fluorophenyl) piperazine | Chem Bridge | No | No | No | No | ? | A | 6 |
| 6785396 | 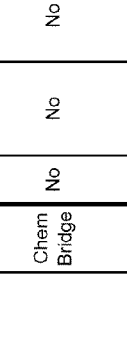 | $C_{24} H_{33} N_3 \cdot C_2 H_2 O_4$ | no | 453.6 | 1-phenyl-4-[1-(3-phenylpropyl)-4-piperidinyl] piperazine oxalate | Chem Bridge | No | No | No | Yes (168) | ? | A | 7 |
| 5422765 | 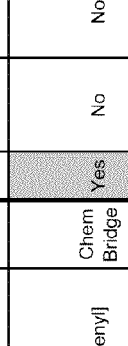 | $C_{19} H_{21} F_3 N_2$ | no | 334.4 | 1-(2-phenylethyl)-4-[3-(trifluoromethyl) phenyl] piperazine | Chem Bridge | Yes | No | No | Yes (130) | ? | A* | 8 |
| 5230300 | 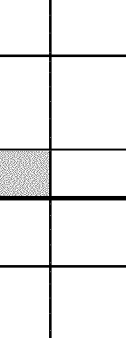 | $C_{42} H_{40} N_2 \cdot 2 Cl H$ | no | 645.7 | N,N,N',N'-tetrakis (3-phenyl-2-propyn-1-yl)-1,6-hexanediamine dihydrochloride | Chem Bridge | No | No | No | No | ? | A | 9 |
| 5230313 | 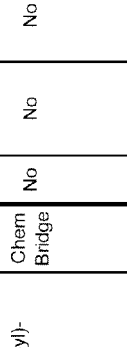 | $C_{28} H_{44} N_2 \cdot 2 Cl H$ | no | 481.6 | 3,3'-(1,4-phenylene) bis (N,N-dibutyl-2-propyn-1-amine) dihydrochloride | Chem Bridge | Yes | No | No | Yes (366) | ? | A* | 10 |

FIG. 14 (continued)
| | 11 | 12 | 13 | 14 | 15 | 16 |
|---|---|---|---|---|---|---|
| | | | | | | plate C |
| | B/C* | B | B/C | C* | B/C | A* |
| | ? | ? | ? | ? | ? | ? |
| | Yes (16.7) | Yes (3.6) | Yes (8.9) | Yes (131.9) | Yes (17.1) | Yes (192.2) |
| | Yes (31.25) | Yes (125) | Yes (125) | No | No | No |
| | Yes (15.625) | Yes (125) | Yes (1.95) | Yes (500) | Yes (125) | (No) |
| | Yes | No | No | Yes | No | Yes |
| | Chem Div | Chem Div | Chem Div | Chem Bridge | Chem Div | Chem Bridge |
| | | | | 4-[3-(4-benzyl-1-piperazinyl)-1-propen-1-yl]-N,N-dimethylaniline | | N,N-diethyl-4-({4-[3-(trifluoromethyl)phenyl]-1-piperazinyl}methyl)aniline |
| | n/a | n/a | n/a | | n/a | |
| | 401.6 | 408.7 | 378.5 | 335.5 | 294.3 | 391.5 |
| | yes | no | yes | (yes) | no | no |
| | $C_{26}H_{29}N_2S$ | $C_{28}H_{44}N_2$ | $C_{27}H_{24}NO$ | $C_{22}H_{29}N_3$ | $C_{19}H_{15}FO_2$ | $C_{22}H_{28}F_3N_3$ |
| | 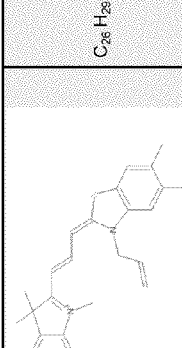 | 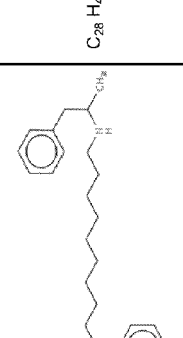 | 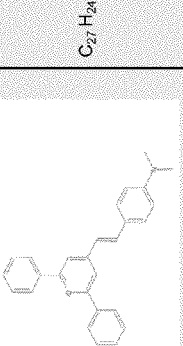 | 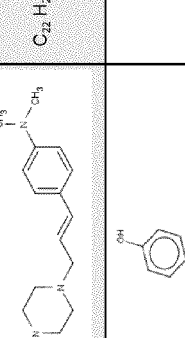 | 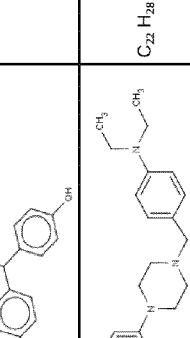 | 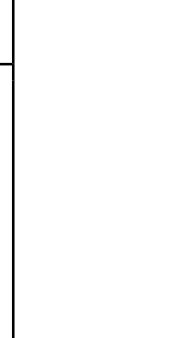 |
| | 7771-0701 | 8006-3639 | 1499-1221 | 5429346 | 0251-0215 | 5427129 |

FIG. 14 (continued)

| | | | | | | | | | | Date D |
|---|---|---|---|---|---|---|---|---|---|---|
| 4636-0141 | 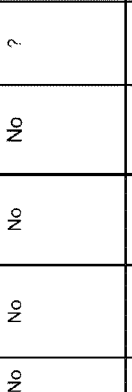 | $C_{19}H_{28}NO$ | no | 284.4 | (4-hydroxybut-2-yn-1-yl) (3-phenylprop-2-yn-1-yl) dipropylazanium | Chem Div | No | No | No | No | ? | A | 17 |
| 5100015 | 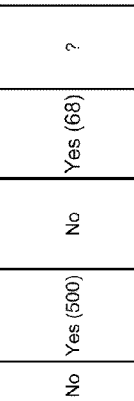 | $C_{21}H_{16}O$ | no | 284.4 | pentacyclo [6.6.0~2,7~.0~9,14~.0~15,20~]icosa- 2,4,6,9,11,13,15,17,19- nonaen-4-ylmethanol | Chem Bridge | No | Yes (500) | No | Yes (68) | ? | B/C | 18 |
| 0438-0367 |  | $C_{14}H_{20}F_2O_4S_4$ | no | 418.6 | 2-({2,5-difluoro-3,4,6-tris[(2-hydroxyethyl)sulfanyl]phenyl}sulfanyl)ethan-1-ol | Chem Div | No | No | No | No | ? | A | 19 |
| N050-0022 |  | $C_{27}H_{46}O$ | no | 386.7 | 2,15-dimethyl-14-(6-methylheptan-2-yl) tetracyclo [8.7.0.0~2,7~.0~11,15~] heptadec-7-en-5-ol | Chem Div | No | No | No | Yes (122.9) | ? | A | 20 |
| 5607-0206 | 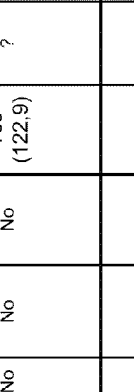 | $C_{22}H_{28}FN_3$ | no | 353.5 | 1-{1-[(2-fluorophenyl) methyl]piperidin-4-yl}-4-phenylpiperazine | Chem Div | No | No | No | No | ? | A | 21 |

| | | | | | | | | | | plate 1 |
|---|---|---|---|---|---|---|---|---|---|---|
| | | | | | | | | | | 29 |
| 7411164 | | $C_{14}H_{20}F_2O_4S_4$ | no | 418.6 | 2,2',2'',2'''-[(3,6-difluorobenzene-1,2,4,5-tetrayl)tetrakis(thio)]tetraethanol | Chem Bridge | No | No | No | No | ? | A |
| 4431/1 | | $C_{22}H_{23}N_2$ | No | 315.4 | 1,3,3-trimethyl-2-(2-(2-methyl-1H-indol-1-yl)vinyl)-3H-1$\lambda^5$-indole | NCI | No | Yes (250) | No | No | ? | C |
| 55870/1 | | $C_{23}H_{21}NO$ | No | 327.4 | N,N-dimethyl-4-(2-phenyl-4H-chromen-4-yl)aniline | NCI | Yes | Yes (250) | No | Yes (25,9) | ? | C* |
| 35487/2 | | $C_{24}H_{28}N_2O$ | No | 360.5 | 2,2-bis(4-(dimethylamino)phenyl)-1-phenylethanol | NCI | No | No | No | No | ? | A |

(Column headers from left: 31, 32, 33 for remaining rows)

FIG. 14 (continued)

| ID | Structure | Formula | | Mass | Name | Source | | | | | | # | Class |
|---|---|---|---|---|---|---|---|---|---|---|---|---|---|
| 96932/4 | 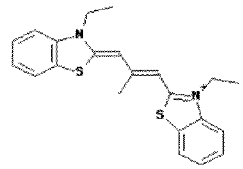 | $C_{22}H_{23}N_2S_2$ | Yes | 379.6 | 3-ethyl-2-(3-(3-ethyl-1,3-benzothiazol-2(3H)-ylidene)-2-methyl-1-propenyl)-1,3λ⁵-benzothiazole | NCI | No | Yes (15,6) | Yes (15.625) | Yes (19) | ? | 34 | B |
| 625586/1 | 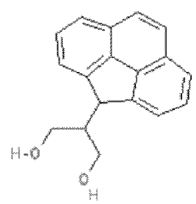 | $C_{18}H_{16}O_2$ | No | 264.3 | 2-(4H-cyclopenta[def]phenanthren-4-yl)-1,3-propanediol | NCI | No | No | No | Yes (83,8) | ? | 35 | A |
| 610995/1 | 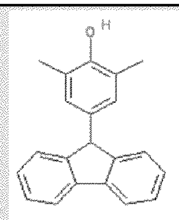 | $C_{21}H_{18}O$ | No | 286.4 | 4-(9H-fluoren-9-yl)-2,6-dimethylphenol | NCI | Yes | Yes (125) | No | Yes (9,2) | ? | 36 | B/C* |
| 290437/2 | 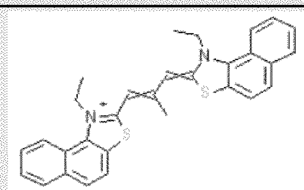 | $C_{30}H_{27}N_2S_2$ | Yes | 479.7 | 1-ethyl-2-(3-(1-ethylnaphtho[1,2-d][1,3]thiazol-2(1H)-ylidene)-2-methyl-1-propenyl)-1λ⁵-naphtho[1,2-d][1,3]thiazole | NCI | No | Yes (1,95) | Yes (31.35) | Yes (2,2) | ? | 37 | B/C |
| 4090-1978 | 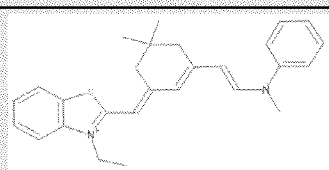 | $C_{27}H_{31}N_2S$ | Yes | 415.6 | 2-{[(1E)-5,5-dimethyl-3-[(E)-2-[methyl(phenyl)amino]ethenyl]cyclohex-2-en-1-ylidene]methyl}-3-ethyl-1,3-benzothiazol-3-ium | Chem Div | No | Yes (15,625) | Yes (62,5) | Yes (16,7) | ? | 38 | B/C |

FIG. 14 (continued)

| | | | | | | | | | | | | | plate 2 |
|---|---|---|---|---|---|---|---|---|---|---|---|---|---|
| 2332-1014 | (structure) | C$_{47}$H$_{37}$N$_5$S$_2$ | Yes | 750.0 | n/a | | Chem Div | No | Yes (62.5) | No | Yes (22,6) | ? | B/C | 39 |
| 4890-0291 | (structure) | C$_{26}$H$_{30}$N$_3$O S | Yes | 432.6 | n/a | | Chem Div | No | Yes (7,81) | Yes (62.5) | Yes (10,7) | ? | B/C | 40 |
| 4121-0081 | (structure) | C$_{14}$H$_{12}$O | No | 196.2 | 9H-fluoren-9-ylmethanol | | Chem Div | No | No | No | Yes (201,8) | ? | A | 41 |
| C611-0808 | (structure) | C$_{20}$H$_{15}$FN$_2$O$_2$S | No | 366.4 | n/a | | Chem Div | No | No | No | No | ? | A | 42 |
| 3377-0105 | (structure) | C$_{26}$H$_{23}$NO | No | 365.5 | 4-[(2,6-diphenyl-4H-pyran-4-ylidene)methyl]-N,N-dimethylaniline | | Chem Div | No | Yes (500) | No | Yes (100,4) | ? | A/B | 43 |

FIG. 14 (continued)

| | 44 | 45 | 46 | 47 | 48 |
|---|---|---|---|---|---|
| plate | | | plate 3 | | |
| ID | 2331-0475 | 7771-0699 | 7771-0716 | 7771-0700 | 7165-0606 |
| Structure | (structure) | (structure) | (structure) | (structure) | (structure) |
| Formula | $C_{34}H_{32}N_2O_2$ | $C_{24}H_{25}N_2S$ | $C_{25}H_{27}N_2OS$ | $C_{25}H_{27}N_2OS$ | $C_{24}H_{25}N_2S$ |
| | No | Yes | Yes | Yes | Yes |
| MW | 500.6 | 373.5 | 403.6 | 403.6 | 373.5 |
| | n/a | n/a | n/a | n/a | n/a |
| Source | Chem Div | Chem Div | Chem Div | Chem Div | Chem Div |
| | No | No | No | No | No |
| | No | Yes (7,8) | Yes (15,625) | Yes (7,8) | Yes (7,8) |
| | No | Yes (125) | Yes (125) | Yes (62,5) | Yes (31,25) |
| | No | Yes (7,9) | Yes (5,3) | Yes (3,7) | Yes (11,9) |
| | ? | ? | ? | ? | ? |
| | A | B | B | B | B |

FIG. 14 (continued)

| | 49 | 50 | 51 | 52 | 53 |
|---|---|---|---|---|---|
| plate 4 | | | | | |
| | B | A* | A | | A |
| | ? | ? | ? | ? | ? |
| | Yes (6,7) | Yes (101,2) | No | Yes (4,2) | Yes (72,1) |
| | Yes (125) | No | No | No | No |
| | Yes (7,8) | No | No | Yes (3,9) | No |
| | No | Yes | No | No | No |
| | Chem Div | Chem Div | Chem Div | Chem Div | Chem Div |
| | n/a | 5-(diphenylamino)-2,3-diphenyl-1,2S!^{5},4-thiadiazol-2-ylium | (5E)-3-phenyl-2-sulfanylidene-5-{2-[(2E)-1,3,3-trimethyl-2,3-dihydro-1H-indol-2-ylidene]ethylidene}-1,3-thiazolidin-4-one | 2-{2,3,5,6-tetrafluoro-4-[2,3,5,6-tetrafluoro-4-(2-hydroxyphenoxy)phenyl]phenoxy}phenol | 1-ethyl-3,3-bis(4-hydroxyphenyl)-2,3-dihydro-1H-indol-2-one |
| | 439.6 | 406.5 | 392.5 | 514.3 | 345.4 |
| | No | No | Yes | No | No |
| | $C_{27}H_{23}N_2S_2$ | $C_{26}H_{20}N_3S$ | $C_{22}H_{20}N_2OS_2$ | $C_{24}H_{10}F_8O_4$ | $C_{22}H_{19}NO_3$ |
| 7165-0758 | | | | | |
| 1492-0330 | | | | | |
| 2101-0102 | | | | | |
| 1611-0203 | | | | | |
| 4896-3423 | | | | | |

FIG. 14 (continued)

| | | | | | | | | plate 5 | |
|---|---|---|---|---|---|---|---|---|---|
| | | | | | | | | 54 | |
| | | | | | | | | | ? |
| 5660386 | ![structure] | $C_{23}H_{25}ClN_2O_4S$ | Yes | 461.0 | 3-ethyl-2-[(1E)-3-[(2Z)-1,3,3-trimethyl-2,3-dihydro-1H-indol-2-ylidene]prop-1-en-1-yl]-1,3-benzothiazol-3-ium perchlorate | Chem Bridge | No | Yes (7,8) | Yes (125) | Yes (5,6) | ? |
| STK 874226 | ![structure] | $C_{22}H_{23}N_2O_2S$ | Yes | 379.5 | 2-[(1E,3E)-4-[acetyl(phenyl)amino]buta-1,3-dien-1-yl]-3-ethyl-6-methoxy-1,3-benzothiazol-3-ium | VitasM Lab | No | Yes (125) | Yes (250) | No | ? |
| 5119716 | ![structure] | $C_{30}H_{33}IN_2OS$ | Yes | 596.6 | 2-[(1E)-3-[(1E)-5,5-dimethyl-3-[(E)-2-(N-phenylacetamido)ethenyl]cyclohex-2-en-1-ylidene]prop-1-en-1-yl]-3-ethyl-1,3-benzothiazol-3-ium iodide | Chem Bridge | No | Yes (125) | No | Yes (52,7) | ? |
| 5100004 | ![structure] | $C_{21}H_{14}O$ | No | 282.3 | pentacyclo[6.6.6.0^{2,7}.0^{9,14}.0^{15,20}]icosa-2,4,6,9,11,13,15,17,19-nonaene-4-carbaldehyde | Chem Bridge | No | No | No | No | ? | A |
| 5190620 | ![structure] | $C_{20}H_{14}O_2$ | (Yes) | 286.3 | pentacyclo[6.6.6.0^{2,7}.0^{9,14}.0^{15,20}]icosa-2(7),3,5,9,11,13,15,17,19-nonaene-3,6-diol | Chem Bridge | No | Yes (62,5) | No | Yes (3,7) | ? |

FIG. 14 (continued)

| | | | | | | | | 9 |
|---|---|---|---|---|---|---|---|---|
| | | | | | | | | 59 |
| | | | | | | | | A |
| | | | | | | | | ? |
| | | | | | | | | Yes (4,4) |
| | | | | | | | | No |
| | | | | | | | | Yes (15,625) |
| | | | | | | | | No |
| | | | | | | | | Chem Bridge |
| | | | | | | | | 1-benzyl-3,3-bis (4-hydroxy-3-methylphenyl)-2,3-dihydro-1H-indol-2-one |
| | | | | | | | | 435.5 |
| | | | | | | | | No |
| | | | | | | | | $C_{29}H_{25}NO_3$ |
| 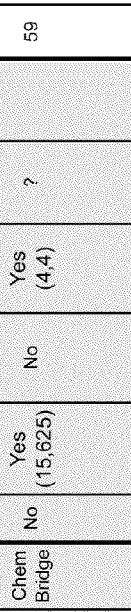 | | | | | | | | |
| 5142587 | | | | | | | | |

Row 60: A, ?, No, No, No, No, Chem Bridge, 3-benzyl-3-hydroxy-2-[(4-methylphenyl)methyl]-2,3-dihydro-1H-isoindol-1-one, 343.4, No, $C_{23}H_{21}NO_2$, 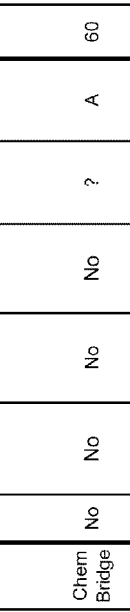, 7832238

Row 61: A, ?, No, No, No, No, Asinex, 2-[2-(4-Methoxy-phenyl)-vinyl]-4,6-diphenyl-pyranylium, 365.4, Yes, $C_{26}H_{21}O_2$, , BAS 00138032

Row 62: A, ?, No, No, No, No, Asinex, 2-(4-tert-Butyl-thiazol-2-yl)-5-phenyl-4-(phenyl-hydrazono)-2,4-dihydro-pyrazol-3-one, 403.5, Yes, $C_{22}H_{21}N_5OS$, 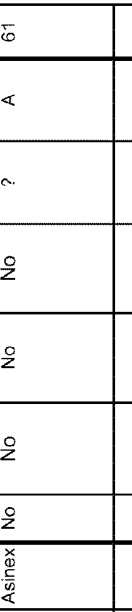, BAS 00691248

Row 63: A, ?, No, No, No, No, Asinex, N-Benzyl-3-(1,3-dimethyl-2-oxo-2,3-dihydro-1H-benzoimidazol-5-yl)-N-(1-methyl-piperidin-4-yl)-propionamide, 420.6, No, $C_{25}H_{32}N_4O_2$, 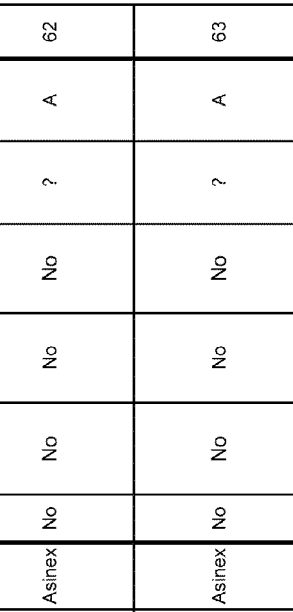, SYN 22879441

FIG. 14 (continued)

| | | | | | | | | | | | plate |
|---|---|---|---|---|---|---|---|---|---|---|---|
| ST 4098270 | | C$_{32}$ H$_{27}$ N$_3$ O S | No | 501.7 | 1-(1,2,3,4-tetrahydroquinolin-1-yl)-2-[(1,4,5-triphenyl-1H-imidazol-2-yl)sulfanyl]ethan-1-one | Tim Tec | No | No | No | No | ? | A | 64 |
| STK 792971 | | C$_{32}$ H$_{35}$ N$_2$ S$_2$ | Yes | 511.8 | 3-ethyl-2-[(E)-{3-[(1E,3E,5Z)-5-(3-ethyl-1,3-benzothiazol-2(3H)-ylidene)penta-1,3-dien-1-yl]-5,5-dimethylcyclohex-2-en-1-ylidene}methyl]-1,3-benzothiazol-3-ium | VitasM Lab | No | Yes (62.5) | No | No | ? | C | 65 |
| STK 537076 | | C$_{25}$ H$_{24}$ N$_4$ S | No | 448.6 | (2E)-2-[4-(2,4-dimethylphenyl)-1,3-thiazol-2-yl]-3-[(9-ethyl-9H-carbazol-3-yl)amino]prop-2-enenitrile | VitasM Lab | No | No | No | Yes (240) | ? | A | 66 |
| STL05007 2 | | C$_{24}$ H$_{28}$ N$_3$ O$_2$ | No | 390.5 | 3-(4-methoxyphenyl)-1-[2-oxo-2-[phenyl(propan-2-yl)amino]ethyl]-1,5,6,7-tetrahydropyrrolo[1,2-a]imidazol-4-ium | VitasM Lab | Yes | No | No | Yes (340) | ? | A | 67 |
| STK 368153 | | C$_{25}$ H$_{21}$ N$_2$ S$_2$ Se$_2$ | Yes | 571.5 | 3-ethyl-2-[(1E,3E)-3-(3-ethyl[1]benzoselenopheno[2,3-d][1,3]thiazol-2(3H)-ylidene)prop-1-en-1-yl][1]benzoselenopheno[2,3-d][1,3]thiazol-3-ium | VitasM Lab | Yes | Yes (7,8) | Yes (7,8) | Yes (9,6) | ? | B* | 68 |

FIG. 14 (continued)

| | | plate 7 | | |
|---|---|---|---|---|
| | 69 | 70 | 71 | 72 |
| | C* | B/C* | A* | B/C* |
| | ? | ? | ? | ? |
| | No | Yes (3.5) | Yes (208,6) | Yes (143,3) |
| | No | No | No | No |
| | Yes (3,9) | Yes (3,9) | No | Yes (125) |
| | Yes | Yes | Yes | Yes |
| | NCI | NCI | NCI | Chem Div |
| | 9-anthryl(1-naphthyl)methanol | n/a | n/a | 5-(diphenylamino)-2,3-diphenyl-1,2$l^{5}$(5),4-thiadiazol-2-ylium |
| | 334.4 | 410.9 | 236.3 | 406.5 |
| | No | No | No | No |
| | $C_{25}H_{18}O$ | $C_{27}H_{19}Cl O_2$ | $C_{17}H_{16}O$ | $C_{26}H_{20}N_3 S$ |
| | | | | |
| | 179415/1 | 363003/1 | 55266/1 | 1492-0330 |

FIG. 14 (continued)

| ID | Structure | Formula | | Name | Source | | | | | | Plate 8 | | |
|---|---|---|---|---|---|---|---|---|---|---|---|---|---|
| | | | | | | | | | | | 73 | 74 | 75 | 76 |
| 5107930 | | $C_{29}H_{33}IN_2S$ | Yes | 568.6 | 2-[(1E)-3-[(1E)-5,5-dimethyl-3-[(E)-2-[methyl(phenyl)amino]ethenyl]cyclohex-2-en-1-ylidene]prop-1-en-1-yl]-3-ethyl-1,3-benzothiazol-3-ium iodide | Chem Bridge | Yes | Yes (31.25) | Yes (125) | Yes (27.9) | ? | B/C* |
| 4090-1979 | | $C_{25}H_{33}N_2S$ | Yes | 393.6 | n/a | Chem Div | Yes | Yes (62.5) | No | Yes (46.2) | ? | B/C* |
| 1493-0289 | | $C_{23}H_{32}NO$ | Yes | 338.5 | 2,6-di-tert-butyl-4-[(E)-2-[4-(dimethylamino)phenyl]ethenyl]-1$l^{4}$-pyran-1-ylium | Chem Div | Yes | Yes (3.9) | Yes (125) | Yes (6.8) | ? | B/C* |
| BAS 00127538 | | $C_{31}H_{28}NO$ | Yes | 430.6 | 2,4-diphenyl-6-[(1E)-3-[(2E)-1,3,3-trimethyl-2,3-dihydro-1H-indol-2-ylidene]prop-1-en-1-yl]-1$l^{4}$-pyran-1-ylium | Asinex | Yes | Yes (1.95) | Yes (7.8) | Yes (2.7) | ? | B/C* | total amount 75 + DMSO

All concentrations are in μM

FIG. 14 (continued)

| *Compound category | |
|---|---|
| A | Not effective compound<br>Not active against S.aureus<br>Not active or active against E.coli<br>Not toxic or toxic for tested cell lines |
| B | Effective but not specific<br>Highly active against S.aureus<br>Highly active against E.coli<br>Toxic for tested cell lines |
| C | Effective and specific, antibiotic candidate<br>Highly active against S.aureus<br>less active against E.coli<br>Not (strong) toxic for tested cell lines |
| * | Lipid II binding |

$IC_{100\%}$ Inhibitory concentration on which 100% killing of bacteria occured, determinded by no bacterial regrowth after exposure to the compound

DEFENSIN-LIKE MOLECULES AS NOVEL ANTIMICROBIAL AGENTS

RELATED APPLICATION

This application is a continuation-in-part of U.S. application Ser. No. 13/883,564 which is a National Stage application of PCT/US11/59432 filed on Nov. 4, 2011, which claims the benefit of U.S. Provisional Application No. 61/410,112 filed on Nov. 4, 2010. This application claims the benefit of U.S. Provisional Application No. 61/656,039 filed on Jun. 6, 2012. The entire contents of each of these applications are hereby incorporated by reference in their entirety.

STATEMENT REGARDING FEDERALLY SPONSORED RESEARCH

This invention was made with government support under Grant Number AI092033 awarded by the National Institutes of Health. The government has certain rights in the invention.

FIELD

The present invention generally relates at least to the fields of microbiology, molecular biology, infectious disease and medicine. In particular, the invention relates to defensin-like molecules and derivatives and analogs thereof for treating and/or preventing infections in mammals.

BACKGROUND

Despite the large numbers of effective antibiotics in use today, patients are increasingly developing infections caused by multidrug-resistant (MDR) pathogens. The emergence of resistance is particularly acute in a clinical setting because of the heavy use of antibiotics. As a consequence of the widespread use of antibiotics, there currently are few if any compounds in clinical use against which resistance has not developed.

The ever increasing emergence of many relevant pathogenic strains of bacteria resistant to commonly used antibiotics is a rapidly growing concern in public health. Patients with weakened immunity because of chemotherapy, AIDS or organ transplantation or patients undergoing acute care in hospitals are significantly at risk for acquiring opportunistic bacterial infections. Strategies to find novel antimicrobial (antibacterial) compounds using bacterial genomics approaches have as yet proven largely unsuccessful.

Seven leading groups of pathogens account for the increased risk for such infections, including Gram-positive bacteria: *Staphylococcus aureus, Enterococcus faecium*, streptococci, and coagulase-negative staphylococci. Resistance against commonly used classical antibiotics has emerged in all of these pathogens.

Given the increasing rate at which infectious organisms develop resistance to antibiotics currently in use, there is an urgent need to develop novel classes of potent antibiotics against molecular targets, such as lipid II. Lipid II is an ideal target for antibiotics because it is an essential component in bacterial cell wall synthesis. Biosynthesis of the bacterial membrane is a classical target for antibiotic development. Lipid II is an essential precursor for bacterial cell wall biosynthesis and an ideal and validated target for natural antibiotic compounds. No synthetic compounds that interfere with Lipid II have yet been developed.

SUMMARY

According to non-limiting example embodiments, the present invention relates to defensin-like molecules for treating and/or preventing infections with microorganisms in mammals including humans and applications for veterinary use.

According to example embodiments, the present invention relates to antimicrobial defensin-like molecules selected from the group comprising the following compounds herein disclosed: 4090-1979; 4090-1978; 4890-0291; BAS00127538; 1493-0289; 1492-0330; and 1611-0203, and derivatives and analogs of these compounds. Example embodiments also relate to compositions that include one or more of such molecules or derivatives or analogs thereof. Further examples relate to kits that include one or more of the present defensin-like molecules or derivatives or analogs thereof, or compositions including the same, and instructions for their use in treating and/or preventing infections in mammals.

According to example embodiments, the present invention relates to methods of treating and/or preventing infections in mammals caused by microorganisms, such as gram-positive bacteria, by administering to the mammal, a therapeutically effective amount for treating and/or preventing such infections, of one or more defensin-like molecules selected from 4090-1979; 4090-1978; 4890-0291; BAS00127538; 1493-0289; 1492-0330; and 1611-0203 and derivatives or analogs thereof. The defensin-like molecules bind to lipid II in bacterial membranes and cause death of a bacterial population. Examples of such bacteria may include for example, one or more of *Staphylococcus aureus, Streptococcus pyogenes, Streptococcus agalactiae, Streptococcus anginosus* group, and *Enterococcus faecalis, Enterococcus faecium* and *Bacillus anthracis*.

Further embodiments are directed to use of the presently disclosed defensin-like molecules or derivatives or analogs thereof, for the prevention or treatment of one or more infections, such as infections caused by bacteria, in particular, gram positive bacteria.

According to further example embodiments, the invention relates to methods of treating and/or preventing sepsis in mammals, by administering to the mammal, a therapeutically effective amount of one or more defensin-like molecules selected from 4090-1979; 4090-1978; 4890-0291; BAS00127538; 1493-0289; 1492-0330; and 1611-0203 and derivatives or analogs thereof.

In other embodiments, the present invention relates to methods for killing a bacterial population or for preventing a bacterial infection comprising administering to a mammalian host infected with said bacterial population a therapeutically effective amount of at least one defensin-like molecule disclosed herein or derivative or analog thereof, or by administering a composition containing the same. By way of example, such methods may include administering to a mammalian host a therapeutically effective amount of at least one of the following molecules 4090-1979; 4090-1978; 4890-0291; BAS00127538; 1493-0289; 1492-0330; and 1611-0203 and derivatives or analogs thereof; or administering to the mammalian host a composition that includes any of these molecules and derivatives or analogs thereof.

BRIEF DESCRIPTION OF THE FIGURES

Non-limiting example embodiments are described herein, with reference to the following accompanying Figures:

FIG. 1 depicts (A) Crystal structure-based model of the HNP-1-Lipid II complex obtained with HADDOCK (High Ambiguity Driven biomolecular DOCKing). The HNP-1 dimer is shown in surface representation. (B) Residue Isoleucine 20 of HNP-1 monomer A interacts with Lysine-3 of the Lipid II pentapeptide, whereas Leucine residue 25 of HNP-1 monomer A interacts with D-Ala at position 4. (C) Residues Arginine 15, Isoleucine 20 and Leucine-25 of HNP-1 monomer B interact with γD-Glu-2 and the phosphate/N-acetyl muramic acid moiety of Lipid II.

FIG. 4 shows that the Lipid II pentapeptide does not antagonize the antibacterial activity of HNP-1. Survival curves of *S. aureus* ATCC 29213 exposed to HNP1 (upper panel) at concentrations varying two-fold from 50 to 1.25 μM or to vancomycin (lower panel) at concentrations varying two-fold from 2 to 0.0125 μM. HNP-1 and vancomycin were pre-incubated with D-ala or D-lac at a 1:200 molar ratio for 30 min prior to addition of bacteria.

FIG. 7 depicts (A-Upper panel) analysis of 2D TOCSY spectra collected at 800 MHz of the aromatic region of compound BAS00127538 alone (black) overlaid with spectra of compound bound to Lipid II (red). (B-Lower panel). 2D natural abunance $^{13}C$ HSQC spectrum illustrating the interaction between Lipid II and the compound BAS00127538. BAS00127538 alone (black) is overlaid with a spectrum of compound bound to Lipid II (red). Spectra were collected on a Bruker 800 MHz Avance NMR spectrometer at 25 degrees. Chemical shift changes for Lipid II upon BAS00127538 compound binding suggest that the interaction is occurring at or near the MurNAc moeity of Lipid II.

FIG. 9 depicts Table 1: residues involved in HNP-1 Lipid II contacts.

FIG. 10 depicts Table 2: classification of lead defensin mimetics.

FIG. 11 depicts Table 3: broth microdilution susceptibility testing for lead defensing mimetics and comparators.

FIG. 13 depicts evidence of efficacy of certain compounds according to non-limiting embodiments of the present invention, against bacteria including *Bacillus anthracis*.

FIG. 14 is a table setting forth structural and chemical formulas, as well as names, molecular weight and other characteristics of examples of various compounds including defensin-like compounds within the scope of the present invention.

DETAILED DESCRIPTION

Figure 2:
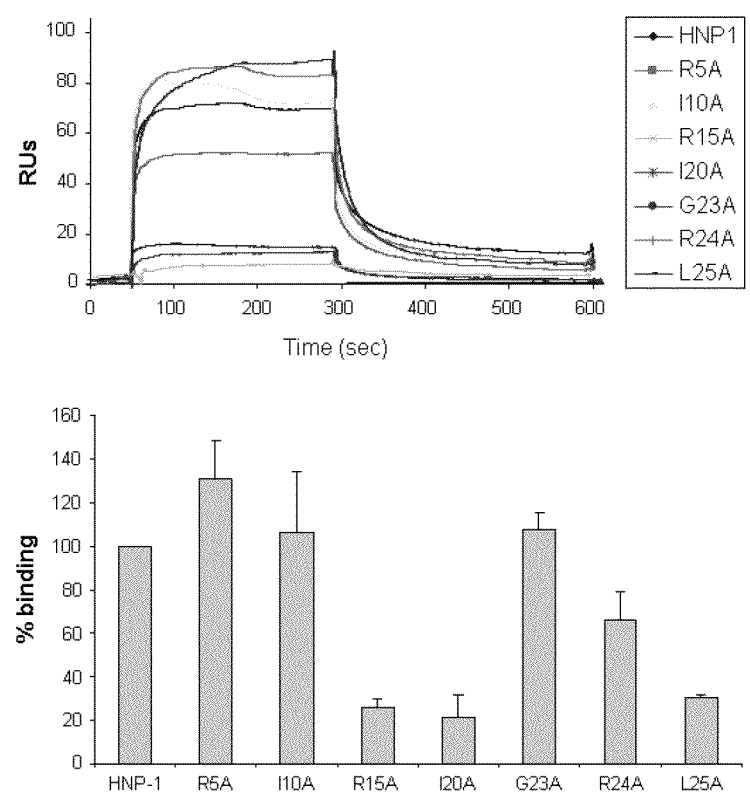
FIG. 2 depicts the following: (Upper panel) Binding of HNP-1 and HNP-1 single alanine mutants on immobilized Lipid II as determined by SPR at room temperature. Representative sensorgrams of one out of two separate experiments of HNP-1 and analogues at 10 μM using a sensorchip with 40 RUs of soluble, 3-Lipid II. (Lower panel) Quantification of binding of HNP-1 mutants compared to binding of wild-type HNP-1, set as 100%.

The present inventors have identified Lipid II as a specific target for killing of Gram-positive bacteria by human defensins. Defensins are important (first line) immune defense molecules and despite being structurally conserved, exert diverse effects at the functional level including binding to lipid II molecules in bacterial cell walls. Molecular modeling can be used to identify defensin-like molecules that mimic naturally occurring antimicrobial products such as antimicrobial defensin peptides as a step toward development of next-generation therapeutic agents for the treatment of bacterial infections, in particular Gram positive bacterial infections.

Every year, an increasing number of people are at risk for bacterial infections that cannot be effectively treated. This is because many bacteria are becoming more resistant to antibiotics. Of particular concern is the rise in hospital-acquired infections. Infection caused by the methicillin-resistant *Staphylococcus aureus* bacterium or MRSA is the cause of many fatalities and puts a burden on health care systems in many countries. The antibiotic of choice for treatment of *S. aureus* infections is vancomycin, an antimicrobial peptide that kills bacteria by binding to the bacterial cell wall component Lipid II. The present inventors have identified for the first time, small synthetic compounds that also bind Lipid II with the aim to develop new antibiotic drugs to fight against bacterial infections.

The discovery and development of novel antibiotic compounds has been slow and the arsenal of effective antibiotics is dwindling. Given the increasing rate at which infectious organisms develop resistance to antibiotics currently in use, there is an urgent need to develop novel classes of potent antibiotics against established molecular targets, such as Lipid II. Lipid II is an essential precursor in cell wall biosynthesis. It is comprised of a hydrophilic head group that includes a peptidoglycan subunit composed of N-acetylglucosamine (GlcNAc) and N-acetylmuramic acid (MurNAc) coupled to a short pentapeptide moiety. This head group is coupled to a long bactoprenol chain via a pyrophosphate group. The amount of Lipid II that can be synthesized is limited and the Lipid II molecule has a high turnover rate, making it an ideal and established molecular target for antibiotics (Labischinski et al, McCloskey at al). Four different classes of peptide antibiotics that target Lipid II have been described: (Gold, H. S., and Moellering, R. C., Jr. (1996) *N Engl J Med* 335, 1445-1453) the glycopeptides, including vancomycin and teicoplanin; the depsipeptide antibiotics, including ramoplanin and enduracidins; the lantibiotics, including nisin and mersacidin and cyclic peptides, including mannopeptimycins, plusbacin and katanosin B.

Recently, defensins were also found to target Lipid II. Defensins represent a major class of antimicrobial peptides found in vertebrates and prominent in mammals (Bevins, C. L. (2006) *Biochem Soc Trans* 34, 263-266; Ganz, T. (2003) *Nat Rev Immunol* 3, 710-720; Lehrer, R. I. (2004) *Nat Rev*

*Microbiol* 2, 727-738; Selsted, M. E., and Ouellette, A. J. (2005) *Nat Immunol* 6, 551-557; and Brogden, et al., (2003) *Int J Antimicrob Agents* 22, 465-478.)

Since the inventors' initial report on the functional interaction of the human defensin peptide HNP1 with Lipid II (de Leeuw, et al.), several studies on defensins from other species has firmly established Lipid II as a target for these peptides. Most notably, Schneider et al (Schneider, T., et al., (2010) *Science* 328, 1168-1172) characterized the Lipid II binding site of the fungal defensin plectasin in molecular detail, putting defensins on the map as clinically relevant antimicrobial peptides. Two additional fungal defensins, oryzeacin (from *Aspergillus oryzae*) and eurocin (from *Eurotium amstelodami*) as well as two invertebrate defensins, lucifensin (from the blowfly *Lucilia sericata*) and gallicin (from the mussel *Mytilus galloprovinciali*), were shown to bind Lipid II in that study (Schneider, et al). More recently, the spectrum of defensins binding Lipid II was widened further to include Human β-Defensin-3 (Sass, V., et al. (2010) *Infect Immun* 78, 2793-2800) and three oyster defensins (Schmitt, P., et al. (2010) *J Biol Chem* 285, 29208-29216).

Strikingly, all of these antimicrobial peptides do not share any obvious sequence- or structural homology, yet all are able to specifically interact with Lipid II in the bacterial membrane environment. The present inventors have determined the unique interaction of HNP-1 with Lipid II. Based on their interaction the inventors further identify small compounds as defensin mimetics and determine their potential as novel antibiotic agents to fight against Gram-positive pathogens. The identified compounds represent the first non-natural, synthetic compounds that bind Lipid II and represent a novel class of molecules that have the potential to be developed into antibiotics that target Lipid II.

The present inventors have identified defensin-like molecules that may be used e.g., to treat or prevent infections in mammals. Therefore, the present invention provides methods of treating and/or preventing infections in mammals, which include administering to a mammal a therapeutically effective amount of at least one defensin-like molecule, or derivative or analog thereof, or administering a therapeutically effective amount of a composition that includes such molecule(s). Those skilled in the art would be able to ascertain, which mammals may be treated by the various methods. For example, the mammal may be human or may be other mammals. Thus, methods of treatment may include for example, veterinary applications.

According to example embodiments, the present invention relates to methods of treating and/or preventing infections caused by microorganisms in particular, such as gram-positive bacteria, by administering to the mammal, a therapeutically effective amount for treating and/or preventing such infections, of one or more defensin-like molecules selected from 4090-1979; 4090-1978; 4890-0291; BAS00127538; 1493-0289; 1492-0330; and 1611-0203 and derivatives or analogs thereof. The defensin-like molecules bind to lipid II in bacterial membranes and cause death of a bacterial population. Examples of such bacteria may include for example, one or more of *Staphylococcus aureus, Streptococcus pyogenes, Streptococcus agalactiae, Streptococcus anginosus* group, *Enterococcus faecalis, Enterococcus faecium* and *Bacillus anthracis*.

According to example embodiments, the present invention relates to antimicrobial defensin-like molecules selected from the group consisting of the following compounds disclosed herein: 4090-1979; 4090-1978; 4890-0291; BAS00127538; 1493-0289; 1492-0330; and 1611-0203, and derivatives and analogs of these compounds. Example embodiments also relate to compositions that include one or more of such molecules. Example compositions may include one or more excipients and may be formulated specifically for administration to a mammal, e.g., for use in the methods herein.

Also provided herein are methods of killing a bacterial population in a mammal or for preventing a bacterial infection that includes administering to a mammal, a therapeutically effective amount for killing or preventing a bacterial population of at least one of the disclosed defensin-like molecules or derivatives or analogs thereof or a composition containing the same. By way of example, such methods may include administering to a mammalian host a therapeutically effective amount of at least one of the following molecules 4090-1979; 4090-1978; 4890-0291; BAS00127538; 1493-0289; 1492-0330; and 1611-0203 and derivatives or analogs thereof; or administering to the mammalian host a composition that includes any of these molecules and derivatives or analogs thereof.

According to further example embodiments, the invention relates to methods of treating and/or preventing sepsis in mammals, by administering to the mammal, a therapeutically effective amount of one or more defensin-like molecules selected from 4090-1979; 4090-1978; 4890-0291; BAS00127538; 1493-0289; 1492-0330; and 1611-0203 and derivatives or analogs thereof. These compounds were tested and proven effective in vivo in a murine model for sepsis.

Also provided are kits that may include one or more of the disclosed molecules or derivatives or analogs thereof, or compositions including such compositions, and instructions for administering said molecules or compositions to a mammal. Such administration may be e.g. for prevention or treatment of a bacterial infection or for the prevention or treatment of sepsis or for other purposes. Kits provided herein may additionally include one or more additional components or excipients that may be used to form a composition for administration of the molecule to a mammal, or one or more tools or components that may be used to administer the composition to a mammal.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

All publications mentioned in this specification are indicative of the level of those skilled in the art to which the invention pertains. All patents and publications herein are incorporated by reference to the same extent as if each individual publication was specifically and individually indicated as having been incorporated by reference in its entirety.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

Defensins form a large subfamily of cationic antimicrobial peptides that kill a broad range of microorganisms Human defensins are cysteine-rich, cationic peptides with molecular masses ranging from 3 to 5 kDa. Based on the connectivity of the six conserved cysteine residues and sequence homology, human defensins are classified into α and β families Both families of defensins have similar three-dimensional structures as determined by X-ray crystallography and NMR studies sharing a common fold of three-stranded anti-parallel β-sheets constrained by three intra-molecular disulfide bonds.

Human defensins were discovered originally as natural peptide antibiotics in neutrophils. These defensins were named Human Neutrophil Peptides (HNP) 1-3 of the α-defensin family. Subsequently, a fourth α-defensin was discovered in neutrophils, termed HNP-4. More recently, two additional α-defensins were described, termed Human Defensin 5 and 6 (Jones, D. E., et al., 1992, "Paneth cells of the human small intestine express an antimicrobial peptide gene," *J Biol Chem* 267:23216-23225; Jones, D. E., and C. L. Bevins, 1993, "Defensin-6 mRNA in human Paneth cells: implications for antimicrobial peptides in host defense of the human bowel," *FEBS Lett* 315:187-192.).

Defensins kill bacteria through pore formation in the microbial membrane, causing leakage of intracellular contents and cell lysis. The specific disruption of the bacterial membrane by defensins is believed to be driven by electrostatic attractions between these cationic peptides and the negatively charged membrane. However, alternative mechanisms for bacterial killing have been proposed, including membrane-independent mechanisms and targeting of intracellular compounds by defensins. (Brogden, K. A, 2005, "Antimicrobial peptides: pore formers or metabolic inhibitors in bacteria?" *Nat Rev Microbiol* 3:238-250; Hancock, R. E., et al., 2002, "Role of membranes in the activities of antimicrobial cationic peptides," *FEMS Microbiol Lett* 206:143-149; Wu, M., et al., 1999, "Mechanism of interaction of different classes of cationic antimicrobial peptides with planar bilayers and with the cytoplasmic membrane of *Escherichia coli*," *Biochemistry* 38:7235-7242.)

Recent observations on the bacterial killing by human defensins could not fully be explained by the membrane-disruption model. First, α-Defensins were shown to preferentially kill Gram-positive bacteria, whereas β-defensins kill Gram-negative strains more effectively (Ericksen, B., et al., 2005, "Antibacterial activity and specificity of the six human {alpha}-defensins,"*Antimicrob Agents Chemother* 49:269-275; Zou, G., E. et al., 2007, "Toward understanding the cationicity of defensins: ARG and LYS versus their non-coded analogs," *J Biol. Chem.*). However, human β-defensins carry more positive charges, indicating that cationicity of defensins alone does not explain this strain-specificity.

Second, disruption of the membrane via stable pore formation is believed to require peptide structure. However, the present inventors and others have shown that bacterial killing by defensins can be structure independent (de Leeuw, E., et al., 2007, "Structure-dependent functional properties of human defensin," 5. *FEBS Lett* 581:515-520; Maemoto, A., et al., 2004, "Functional analysis of the alpha-defensin disulfide array in mouse cryptdin-4," *J Biol Chem* 279:44188-44196.)

Third, the present inventors recently observed that α-defensins composed entirely of D-amino acids show greatly reduced anti-bacterial activity against *Staphylococcus aureus* compared to the L-peptide, suggesting that the microbial membrane is not the sole target (Wei, G., et al., 2009, "Through the looking glass, mechanistic insights from enantiomeric human defensins". *J Biol Chem* 284:29180-29192.)

The present inventors have discovered the interaction between the α-defensin Human Neutrophil Peptide 1 (HNP-1) and lipid II levels in the bacterial membrane and have further discovered particular defensin-like molecules or compounds, which may mimic human defensin and have a similar effect with respect to treating or killing bacterial populations and/or preventing their formation in a mammal.

As indicated above, the present inventors having identified defensin-like molecules that may be used e.g., to treat or prevent infections in mammals. Such molecules may be delivered or administered to a mammal for example, in a composition that includes one or more of such molecules, e.g., in a therapeutically effective amount for treating or preventing infections in a mammal. An effective amount or therapeutically effective amount may be determined by one skilled in the art such as a physician or veterinarian, depending e.g., on the type of mammal, its weight or size, and/or age of the mammal, infection being treated or prevented, etc.

Non-limiting example defensin-like molecules that may be used in the present embodiments may include for example, the following compounds A-H, and derivatives and analogues thereof:

Compound A, 4090-1979 (Chemdiv, 1-C2)

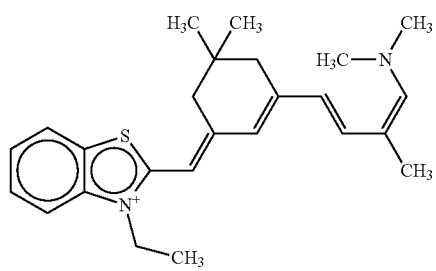

2-{[(1E)-3-[(1E,3Z)-4-(dimethylamino)-3-methylbuta-1,3-dien-1-yl]-5,5-dimethylcyclohex-2-en-1-ylidene]methyl}-3-ethyl-1,3-benzothiazol-3-ium, Compound B, 4090-1978

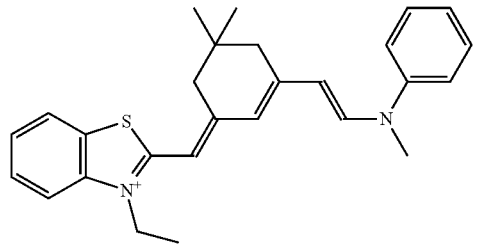 [SMILES: CC[n+]1c(/C=C2C=C(/C=C/N(C)c3ccccc3)CC(C)(C)C/2)sc2ccccc21]

2-{[(1E)-5,5-dimethyl-3-[(E)-2-[methyl(phenyl)amino]ethenyl]cyclohex-2-en-1-ylidene]methyl}-3-ethyl-1,3-benzothiazol-3-ium Compound C, 4890-0291 (Chemdiv, 1-PC1)

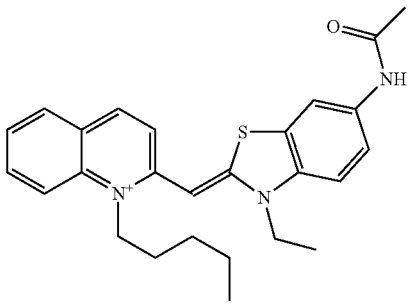 [SMILES: CCCCC[n+]1c(/C=C2\Sc3cc(NC(C)=O)ccc3N2CC)ccc2ccccc21]

N-[(2Z)-3-ethyl-2-[(1-pentylquinolin-1-ium-2-yl)methylidene]-1,3-benzothiazol-6-yl]acetamide Compounds A-C are derivatives of compound 5107930.

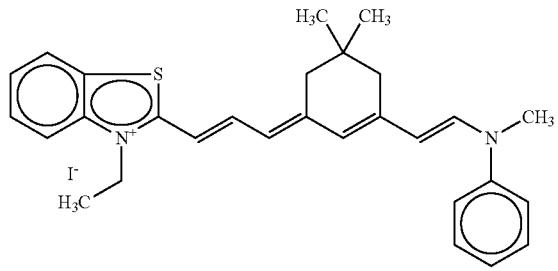

2-[(1E)-3-[(1E)-5,5-dimethyl-3-[(E)-2-[methyl(phenyl)
amino]ethenyl]cyclohex-2-en-1-ylidene]prop-1-en-1-yl]-
3-ethyl-1,3-benzothiazol-3-ium iodide.

Compound D, BAS00127538 (Asinex, 3-PC-2)

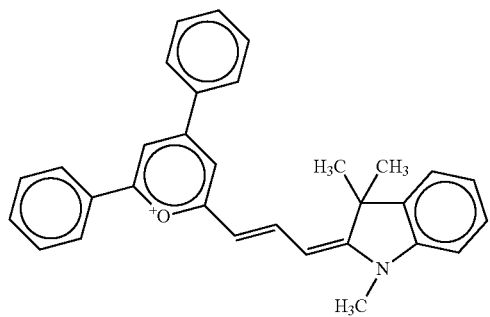

2,4-diphenyl-6-[(1E)-3-[(2E)-1,3,3-trimethyl-2,3-dihydro-
1H-indol-2-ylidene]prop-1-en-1-yl]-1$1^{4}-pyran-1-
ylium Compound E, 1493-0289 (Chemdiv, 3-C-4)

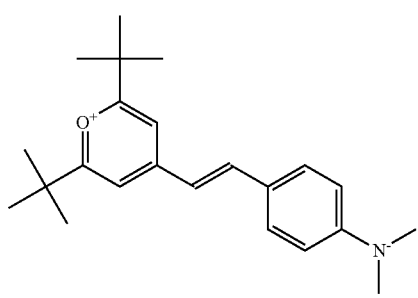

2,6-di-tert-butyl-4-[(E)-2-[4-(dimethylamino)phenyl]ethe-
nyl]-1$1^{4}-pyran-1-ylium Compounds D and E are derivatives of 1499-1221:

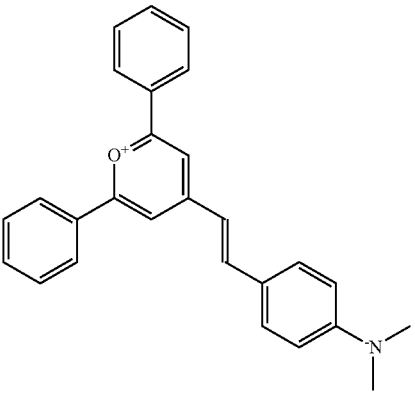

2-[(E)-2-[4-(dimethylamino)phenyl]ethenyl]-4,6-diphenyl-
pyran-3-ylium

Compound F, 1492-0330 (Chemdiv, 4-PC17)

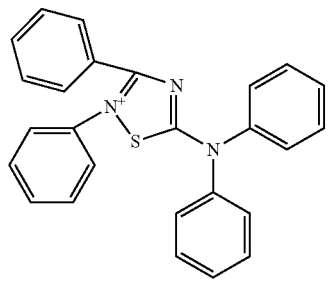 [SMILES: c1ccc(-c2nc(N(c3ccccc3)c3ccccc3)s[n+]2-c2ccccc2)cc1]

5-(diphenylamino)-2,3-diphenyl-1,2$1^{5},4-thiadiazol-2-
ylium

Compound F is a derivative of 7771-0701

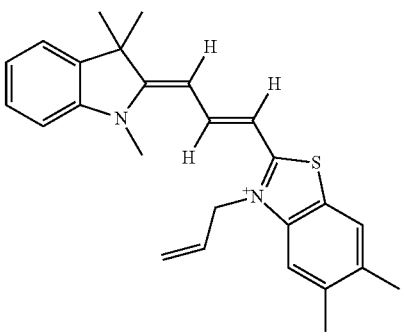 [SMILES: C=CC[n+]1c(/C=C/C=C2\N(C)c3ccccc3C2(C)C)sc2cc(C)c(C)cc21]

5,6-dimethyl-3-prop-2-enyl-2-[(E,3Z)-3-(1,3,3-trimethylin-
dol-2-ylidene)prop-1-enyl]-1,3-benzothiazol-3-ium Compound G, 1611-0203 (Chemdiv, 5-C-96)

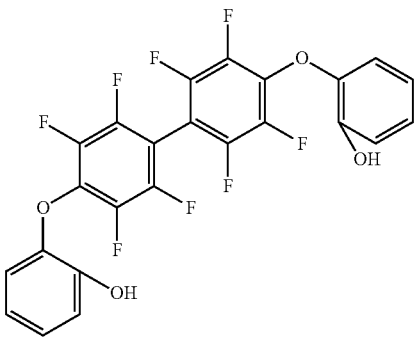 [SMILES: Oc1ccccc1Oc1c(F)c(F)c(-c2c(F)c(F)c(Oc3ccccc3O)c(F)c2F)c(F)c1F]

2-{2,3,5,6-tetrafluoro-4-[2,3,5,6-tetrafluoro-4-(2-hydroxyphenoxy)phenyl]phenoxy}phenol
Compound H, 363003 (NCI, 5-C-12)

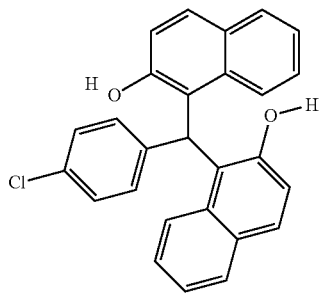

1-[(4-chlorophenyl)(2-hydroxynaphthalen-1-yl)methyl]naphthalen-2-ol
Compounds G and H are derivatives of 0251-0215

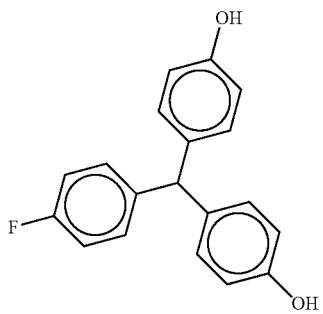

4-[(4-fluorophenyl)(4-hydroxyphenyl)methyl]phenol

Also provided herein are compositions, e.g. for treating or preventing inventions, which include on or more of the above Compounds A-H, i.e., compounds 4090-1979, 4090-1978, 4890-0291, BAS00127538, 1493-0289, 1492-0330 and 1611-0203, or derivatives or analogs thereof.

Further example defensin-like molecules or derivatives or analogs of defensin-like molecules, may include molecules that may be determined based on the present disclosure. Non-limiting examples include defensin-like molecules or derivatives or analogs of defensin-like molecules, which are capable of binding to lipid II in bacterial membranes and cause death of a bacterial population.

Any of the compositions herein may also include one or more pharmaceutically acceptable excipients. Suitable excipients for various types of compositions are well known to those skilled in the art, and suitable excipients may be determined for example based on the desired formulation, e.g., whether the composition is formulated for ingestion and if so, in what form (tablet, capsule, etc), or injection or for another form of administration. Example types of excipients may include for example dyes, flavors, binders, emollients, fillers, lubricants, preservatives, and the like. Example formulations may include e.g., formulations for oral administration or I.V. formulations.

Example embodiments also include methods of treating and/or preventing infections in mammals, such as humans. The infections may be for example, caused by microorganisms or it may be sepsis. Example methods may include administering to the mammal at least one defensin-like molecule, derivative and/or analog thereof as disclosed herein. Further example methods may include administering to a mammal a therapeutically effective amount of at least one of the defensin-like molecules (e.g., compounds A-H) disclosed herein, or derivatives and analogues thereof.

The defensin-like molecules, may be administered to the mammal (either directly or in a composition) in for example a therapeutically effective amount for treating and/or preventing an infection, such as a bacterial infection. The microorganism may be for example, gram positive bacteria. In particular, the bacteria may include one or more bacteria selected from the group consisting of *Staphylococcus aureus, Streptococcus pyogenes, Streptococcus agalactiae, Streptococcus anginosus* group, *Enterococcus faecalis, Enterococcus faecium* and *Bacillus anthracis*.

Example embodiments are directed to the use of a therapeutically effective amount of one or more of the disclosed defensin-like molecules or derivatives or analogs of defensin-like molecules, or compositions that include such defensin-like molecules or derivatives or analogs thereof, for the treatment of or prevention of an infection of microorganisms in a mammal, such as a human. The molecules, compositions, infections, microorganisms, and mammals are as discussed hereinabove with respect to other embodiments. For example, example embodiments are directed to the use of a therapeutically effective amount of one or more of the above-indicated molecules or derivatives or analogs thereof, for the treatment of or prevention of an infection of microorganisms in a mammal.

Also provided herein are methods of preventing and/or killing a bacterial population in a mammal. Such methods may include administering to a mammal, a therapeutically effective amount (for killing and/or preventing infection of a bacterial population in the mammal), of at least one defensin-like molecule, for example, in a composition that includes such molecules. The mammal may be for example a mammal that is infected with at least one bacterial population. The present molecules kill the bacterial population in a mammal by binding to lipid II in bacterial membranes and cause death of the bacterial population.

In the case of methods of preventing a bacterial population, the mammal may be for example a mammal who has been exposed to at least one bacteria. The mammal may be for example a mammal having a reduced immunity (e.g., immune compromised) or in a high risk group for severe reaction or complications if infection were to occur (e.g., infant or elderly), who may or may not have been exposed to at least one bacteria. A physician or veterinarian skilled in the art would be able to determine or decide to which particular mammals, the molecules or compositions should be administered.

Example defensin-like molecules, derivatives and/or analogs thereof (i.e, of defensin-like molecules), are as discussed throughout this application. The microorganism may be for example, gram positive bacteria as discussed above. Thus, as indicated above, examples of the bacterial population may include populations of one or more bacteria selected from the group consisting of *Staphylococcus aureus, Streptococcus pyogenes, Streptococcus agalactiae, Streptococcus anginosus* group, *Enterococcus faecalis, Enterococcus faecium*, and *Bacillus anthracis*.

Provided herein are example kits that may include at least one molecule selected from the group consisting of defensin-like molecules, derivatives, and analogs thereof or components thereof, or at least one composition that includes one or more molecules selected from the group consisting of defensin-like molecules, derivatives, and analogs thereof; and instructions for administering said molecules or compositions to a mammal for prevention or treatment of a bacterial infection.

A mammal in need of such a composition may include for example, a mammal who has already been infected e.g., with a bacterial population, or it may include mammals at increased risk for becoming infected e.g., with a bacterial population (e.g., by exposure and/or immune-compromised), or mammals who may be at higher risk for becoming infected or for complications or severe reaction in the case of becoming infected. A mammal in need of the composition may be determined by one skilled in the art.

As indicated above, kits according to example embodiments, include one or more the present defensin-like molecules or derivatives or analogs thereof, or compositions including the same, and instructions for their use in treating and/or preventing infections in mammals. Example kits provided herein may additionally include for example, one or more additional components or excipients that may be used in the present compositions, and/or one or more tools or components that may be used to administer the composition to a mammal, such as a syringe, etc.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

The following details how the present compounds were discovered for use in the present methods.

Compounds were selected based on selective killing of Gram-positive pathogens, Lipid II binding, and efficacy in an in vivo murine model for sepsis. The inventors have tested some compounds against other pathogens, such as *Bacillus anthrax*.

The present inventors obtained structural information of a complex between defensin and the target, Lipid II. That information was combined with computer modeling to derive all compounds listed in FIG. 14. The compounds were tested for specificity of Gram-positive killing, Lipid II binding and promising ones were further tested in vivo.

A similarity search was done on compounds 5107930, 5100015 (Chembridge) and 1499-1221, 7771-0701, 0251-0215 (Chemdiv), identified after a first search. These compounds were selected based on:

Lipid II binding (Biacore), preferentially killing of *S. aureus* over *E. coli*, using an in-house assay, and cytotoxicity (MTT assays following exposure to human intestinal epithelial cell line Caco-2).

A second round of compounds was identified based on similarity of chemical properties or of physiochemical properties to the five compounds identified in the first search. Selected compounds from this second round were selected based on:

Lipid II binding (Biacore), preferentially killing of *S. aureus* over *E. coli*, both using an in-house assay as well as determination of the MIC according to industry standard, and cytotoxicity (MTT assays following exposure to human intestinal epithelial cell line Caco-2 for 24 hours as well as human Jurkat T cells for 4 hours).

Additionally, interesting lead compounds were tested and proven effective in vivo in a murine model for sepsis. These compounds are: 1) 4090-1979; 2) 4890-0291; 3) BAS00127538*; 4) 1493-0289; 5) 1492-0330; and 6) 1611-0203. *Note: this compound has been found to interact with Lipid II by NMR analysis.

Details of these compounds are listed herein and in the accompanying Figures. Provided herein are their chemical structures and names as well as compounds from which they have been derived. Original compounds that formed the basis for the present compounds are provided herein.

Example 2

This example depicts synthesis of compound BAS00127538 in accordance with non-limiting examples of the present invention.

Scheme 1: A. Synthesis of lead compound BAS00127538 (BF$_4$-salt).
B.-D. Procedures to introduce chemical diversity

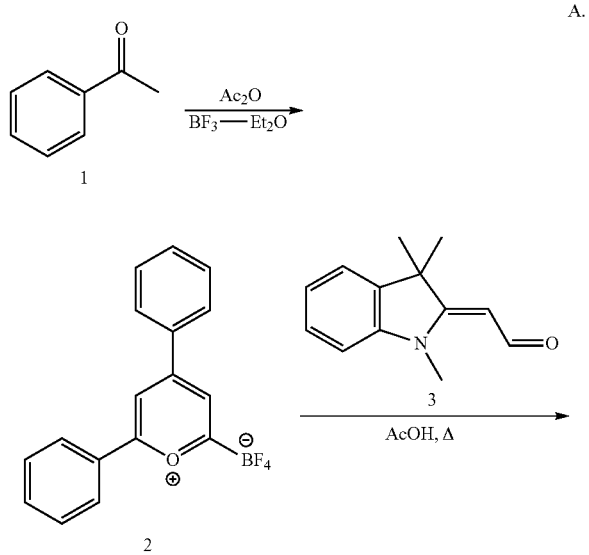

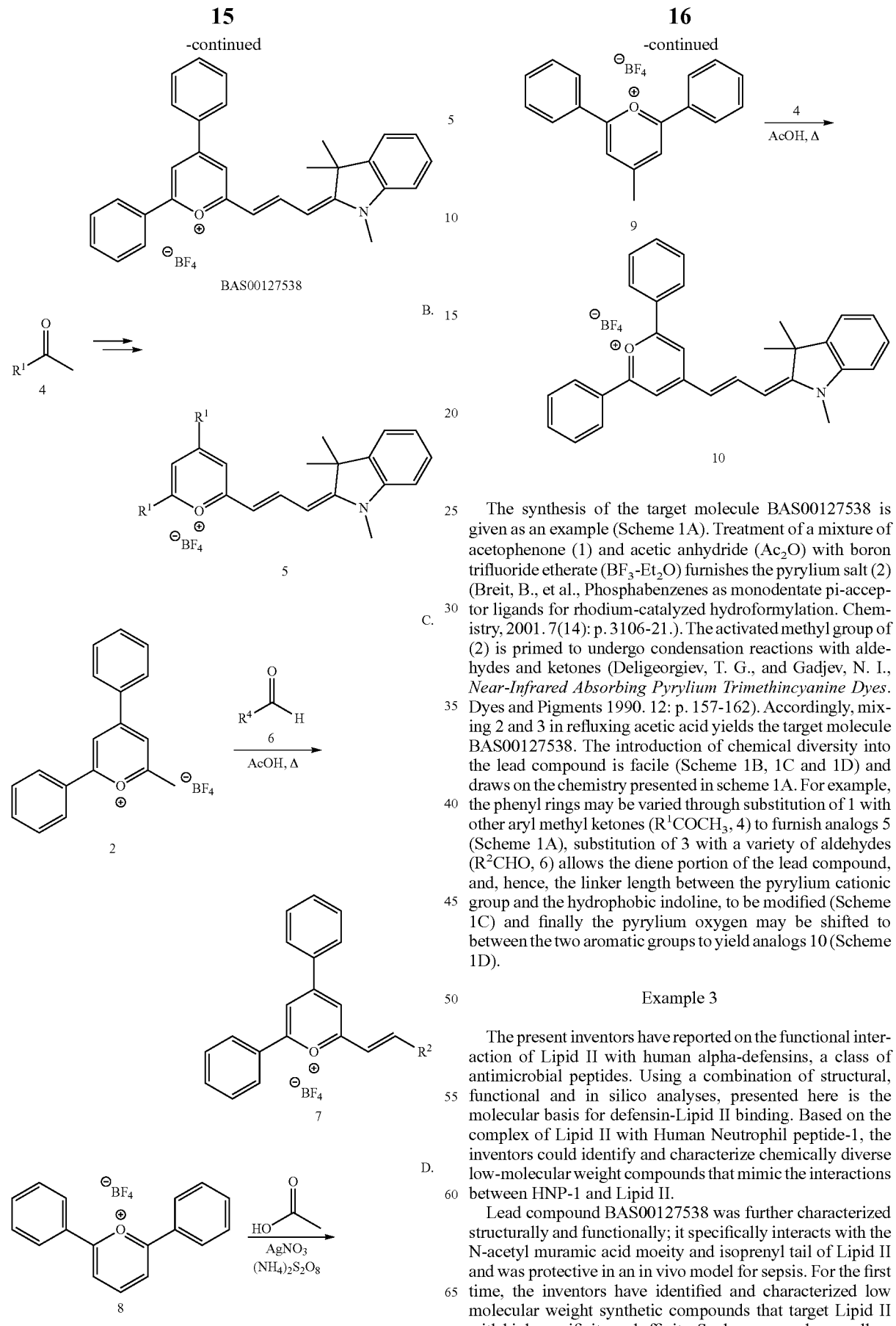

The synthesis of the target molecule BAS00127538 is given as an example (Scheme 1A). Treatment of a mixture of acetophenone (1) and acetic anhydride (Ac$_2$O) with boron trifluoride etherate (BF$_3$-Et$_2$O) furnishes the pyrylium salt (2) (Breit, B., et al., Phosphabenzenes as monodentate pi-acceptor ligands for rhodium-catalyzed hydroformylation. Chemistry, 2001. 7(14): p. 3106-21.). The activated methyl group of (2) is primed to undergo condensation reactions with aldehydes and ketones (Deligeorgiev, T. G., and Gadjev, N. I., *Near-Infrared Absorbing Pyrylium Trimethincyanine Dyes*. Dyes and Pigments 1990. 12: p. 157-162). Accordingly, mixing 2 and 3 in refluxing acetic acid yields the target molecule BAS00127538. The introduction of chemical diversity into the lead compound is facile (Scheme 1B, 1C and 1D) and draws on the chemistry presented in scheme 1A. For example, the phenyl rings may be varied through substitution of 1 with other aryl methyl ketones (R$^1$COCH$_3$, 4) to furnish analogs 5 (Scheme 1A), substitution of 3 with a variety of aldehydes (R$^2$CHO, 6) allows the diene portion of the lead compound, and, hence, the linker length between the pyrylium cationic group and the hydrophobic indoline, to be modified (Scheme 1C) and finally the pyrylium oxygen may be shifted to between the two aromatic groups to yield analogs 10 (Scheme 1D).

Example 3

The present inventors have reported on the functional interaction of Lipid II with human alpha-defensins, a class of antimicrobial peptides. Using a combination of structural, functional and in silico analyses, presented here is the molecular basis for defensin-Lipid II binding. Based on the complex of Lipid II with Human Neutrophil peptide-1, the inventors could identify and characterize chemically diverse low-molecular weight compounds that mimic the interactions between HNP-1 and Lipid II.

Lead compound BAS00127538 was further characterized structurally and functionally; it specifically interacts with the N-acetyl muramic acid moeity and isoprenyl tail of Lipid II and was protective in an in vivo model for sepsis. For the first time, the inventors have identified and characterized low molecular weight synthetic compounds that target Lipid II with high specificity and affinity. Such compounds may allow for their development as novel, next generation therapeutic agents for the treatment of Gram-positive pathogenic infections.

Materials and Methods

Materials

Chemicals used for solid phase peptide synthesis were obtained as described (Wu, Z., Ericksen, B., Tucker, K., Lubkowski, J., and Lu, W. (2004) *J Pept Res* 64, 118-125). *Staphylococcus aureus* ATCC 29213 and *Escherichia coli* ATCC 25922 were obtained from Microbiologics (St. Cloud, Minn.). DiAcetyl-Lys-D-Alanine-D-Alanine (D-Ala), DiAcetyl-Lys-D-Alanine-D-Lac (D-Lac) and vancomycin were purchased from Sigma. Defensin mimetic compounds that were used are listed in FIG. 14.

Solid Phase Peptide Synthesis

Chemical synthesis and folding of defensins was carried out as described (Wu, et al, *J Pept Res* 64, 118-125, Wu, Z., Powell, R., and Lu, W. (2003) *J Am Chem Soc* 125, 2402-2403). The molecular mass of the peptides was verified by electrospray ionization mass spectrometry (ESI-MS) as described (Wu, et al, *J Pept Res* 64, 118-125). Peptide stock solutions prepared with water were quantified spectroscopically using molar extinction coefficients at 280 nm calculated according to the algorithm of Pace et al (Pace, C. N., Vajdos, F., Fee, L., Grimsley, G., and Gray, T. (1995) *Protein Sci* 4, 2411-2423).

Lipid II Purification

Short-chain water-soluble Lipid II containing a lipid tail of three isoprene units was generated and purified essentially as described (Breukink, E., van Heusden, H. E., Vollmerhaus, P. J., Swiezewska, E., Brunner, L., Walker, S., Heck, A. J., and de Kruijff, B. (2003) *J Biol Chem* 278, 19898-19903). Typically, *M. flavus* vesicles (120 μmol lipid-Pi) were incubated together with 500 μmol UDP-GlcNAc, 500 μmol UDP-MurNAC-pentapeptide and 400 μmol farnesyl phosphate (3-P) in 100 mM Tris-HCl pH 8.0, 5 mM $MgCl_2$. The incubation lasted two hours at room temperature for 3-P. The synthesis of 3-Lipid II was followed using RP-8 reversed phase TLC (Merck) developed in 75% methanol. For purification, the membranes were removed by centrifugation at 40,000×g and the supernatant was collected and loaded on a C18 HPLC column and eluted with a linear gradient from 50 mM ammonium bicarbonate to 100% methanol in 30 minutes. Farnesyl-Lipid II (3-Lipid II) eluted at approximately 60% methanol. Its identity was confirmed by mass spectroscopy.

Surface Plasmon Resonance

Surface Plasmon Resonance binding experiments were carried out on a BIAcore T100 system (BIAcore Inc., Piscataway, N.Y.) at 25° C. The assay buffer was 10 mM HEPES, 150 mM NaCl, 0.05% surfactant P20, pH 7.4 (±3 mM EDTA) supplemented with 10% DMSO. 3-Lipid II (50 RUs) was immobilized on CM5 sensor chips using the amine-coupling chemistry recommended by the manufacturer. For initial determination of binding, defensin mimetics were introduced into the flow-cells (30 μl/min) in the running buffer at 10 μM. Resonance signals were corrected for nonspecific binding by subtracting the background of the control flow-cell. After each analysis, the sensor chip surfaces were regenerated with 50 mM NaOH for 30 s at a flow rate 100 μl/min, and equilibrated with the buffer prior to next injection. For binding kinetics studies, binding isotherms were analyzed with manufacturer-supplied software for BIAcore T100.

Antibacterial Activity Assay

The antibacterial activity of defensin mimetics against *Staphylococcus aureus* ATCC 29213 and *Escherichia coli* 25922 was carried out in a 96-well turbidimetric assay essentially as described (Ericksen, B., Wu, Z., Lu, W., and Lehrer, R. I. (2005) *Antimicrob Agents Chemother* 49, 269-275) with the following modifications: compounds were exposed for 30 min to bacteria prior to addition of bacteria in 10 mM phosphate buffer containing 5% DMSO. Bacterial growth was monitored for 12 hours and data were analyzed as described (Ericksen, et al). Determination of MICs was performed by Micromyx, LLC (Kalamazoo, Mich.) according to CLSI standards (CLSI. (2009) *Methods for Dilution Antimicrobial Susceptibility Tests for Bacteria That Grow Aerobically; Approved Standard—Eighth Edition*.)

Antagonization Assays

Antagonization of the antibacterial activity of defensins against *Staphylococcus aureus* ATCC 29213 was carried out in a 96-well turbidimetric assay essentially as described previously (Erickson et al.). Defensins (50 μM final concentration) were pre-incubated with the following compounds for 30 min at RT: 1) 3-Lipid II at 1:1, 1:2.5 and 1:5 defensin:Lipid II molar ratios; or; 2) DiAcetyl-Lys-D-Alanine-D-Alanine and DiAcetyl-Lys-D-Alanine-D-Lac at 1:200 molar ratios. Additionally, vancomycin (500 μM) was pre-incubated separately with D-Ala and D-Lac at a 1:200 molar ratio. Following incubation, solutions were diluted two-fold in ten steps and bacteria were added. Bacterial cells were exposed to HNP1 or vancomycin for 30 min and to HD-5 for 60 min in all studies. Defensin activity was neutralized by the addition of Mueller Hinton broth. Bacterial growth was monitored for 12 hours and data were analyzed as described (Erickson et al.).

Crystallization and Modeling of the HNP-1/Lipid II Complex

Crystallization of the HNP-1/Lipid II complex was carried out by hanging drop vapor diffusion. The partial crystal structure of the complex, in which Lipid II could not be built entirely due to a lack of electron density, was subsequently used for generating a model of the complex by data-driven docking using the HADDOCK program (2.1 version) (Dominguez, C., Boelens, R., and Bonvin, A. M. (2003) *J Am Chem Soc* 125, 1731-1737; de Vries, S. J., van Dijk, A. D., Krzeminski, M., van Dijk, M., Thureau, A., Hsu, V., Wassenaar, T., and Bonvin, A. M. (2007) *Proteins* 69, 726-733). The observed electron density around Ile20 of chain A, Leu25 of both chains and Arg15 of chain B was used to define ambiguous interaction restraints (AIRs) with an upper distance bound of 2 Å between the side-chains of those residues and the soluble part of Lipid II (peptidic tail, oligosaccharide and pyrophosphate group). Random removal of restraints was turned off. One lipid II molecule was docked onto the HNP1 dimer with C2 symmetry restraints defined between the two HNP1 monomers. Topology and parameters for Lipid II were taken from Hsu, S. T., Breukink, E., Tischenko, E., Lutters, M. A., de Kruijff, B., Kaptein, R., Bonvin, A. M., and van Nuland, N. A. (2004) *Nat Struct Mol Biol* 11, 963-967. Lipid II was treated as fully flexible during the refinement stage of HADDOCK. The docking was performed with default parameters, except for an increased number of models, 2000 at the rigid-body docking stage and 400 for subsequent flexible and explicit solvent refinement. The resulting models were clustered using a 7.5 Å RMSD cutoff and the clusters ranked based on the default HADDOCK score.

Computer-Aided Drug Design (CADD)-Database Searching

Identification of Defensin mimetics involved two steps: 1) a 3D pharmacophore fingerprint typed atom triangles (TAT) (Lichtenstein, S. J., Dorfman, M., Kennedy, R., and Stroman, D. (2006) *J Pediatr Ophthalmol Strabismus* 43, 19-26) search and 2) a chemical/physiochemical similarity search with MACCS (Brown, R. D., and Martin, Y. C. (1997) *Journal of Chemical Information and Computer Sciences* 37, 1-9) and MPMFP (Xue, L., Godden, J. W., Stahura, F. L., and Bajorath, J. (2003) *Journal of Chemical Information and Computer*

Sciences 43, 1151-1157) fingerprints performed using the program MOE (Chemical Computing Group Inc.) (Lichtenstein et al.).

The first step was performed to find compounds that can mimic the chemical characteristics and relative spatial arrangement of the HNP-1 residue side chains that are important for binding with Lipid II. The full side chains of Ile20, Leu25 of monomer A and Arg15, Ile20 and Leu25 of monomer B from the experimentally solved complex structure were used as the reference for the pharmacophore search. As only the nitrogens of the Arg side chain serve as hydrogen-bond donors that interact with Lipid II, another reference structure with only the C—$(NH_2)_2$ moiety of the Arg15 side chain along with the full aliphatic side chains of other four key residues was also used for the pharmacophore search.

To prepare compound databases for searching, 3D structures of low-molecular weight compounds were generated from 2D structures obtained from three large commercial databases; Maybridge (Thermo Fisher Scientific Inc., Wattham, Mass.), ChemBridge (San Diego, Calif.), and ChemDiv (San Diego, Calif.), which contain 59676, 482276, and 533143 compounds, respectively. The compounds were converted into 3D structures using MOE and subsequently minimized with the MMFF94 force field (Halgren, T. A. (1996) *Journal of Computational Chemistry* 17, 490-519) to a root-mean-square (RMS) gradient of 0.05 kcal/mol/A, followed by the assignment of 3D pharmacophore fingerprints for similarity searching. Pharmacophore searching was performed by comparing the small molecule 3D fingerprints with the HNP-1 dimer 3D pharmacophores with the extent of overlap calculated based on the Tanimoto similarity indices. (Willett, P., Barnard, J. M., and Downs, G. M. (1998) *Journal of Chemical Information and Computer Sciences* 38, 983-996). Database compounds with a Tanimoto index over selected cutoff values, with physiochemical properties that maximize bioavailability (Lipinski, C. A., Lombardo, F., Dominy, B. W., and Feeney, P. J. (2001) *Adv Drug Deliv Rev* 46, 3-26) and with unique chemical scaffolds were selected for the first round of biological experiments.

A second round of in silico searching was performed to find analogs of the five active compounds identified in the first round of pharmacophore searching and experimental testing. For each active compound, two individual similarity searches were performed to find compounds that are either structurally similar or physiochemically similar to the query compound, using MACCS or MPMFP fingerprints, respectively. An in-house database in the University of Maryland Computer-Aided Drug Design Center with 5.04 million compounds was used for searching. Database compounds with a Tanimoto index over selected cutoff values and with drug-like characteristics that maximize bioavailability (Lipinski et al.) were selected for the second round of biological experiments.

Nuclear Magnetic Resonance

The NMR samples included 0.15 mM Lipid II, 0.15 mM BAS00127538 compound, or 0.15 mM Lipid II+0.15 mM BAS00127538 compound. All samples were dissolved in 90% double distilled $H_2O$+10% DMSO, incubated for 30 minutes, freeze-dried, and then dissolved in 300 uL of d6-DMSO. NMR experiments were carried out at 25° C. on an 800 MHz Bruker Avance NMR spectrometer (800.27 MHz for protons) equipped with a pulse-field gradient unit, four frequency channels, and a triple resonance TXI cryoprobe (Bruker Biospin, Billerica, Mass.). 1D proton experiments were collected to probe for chemical shift changes and 2D TOCSY (30, 60, and 90 msec spinlock times), 2D NOESY (150 and 300 msec mixing times), and natural abundance $^{13}C$-HSQC experiments were collected to determine proton and carbon chemical shift assignments.

Murine Peritoneal Sepsis Model

Adult C57BL/6J mice (~18 grams, 8-10 weeks old) were used for all experiments. Mice were obtained from the Jackson Laboratory (Bar Harbour, Me., USA) and housed in the IHV SPC animal core facility. Mice were fed standard chow (Harlan Laboratories) and water ad libitum. To assess the protective potency of defensin mimetic BAS00127538, groups of 5 mice were inoculated intraperitoneally ~$10^7$ CFU/mL of *S. aureus* ATCC 29213 in 500 μL saline solution/ 25% DMSO plus 4.5% (w/v) porcine gastric mucin (Sigma Chemical Co., St Louis, Mo.). Infected animals (n=5) were subsequently treated by intra-peritoneal injection 1 and 4 hours post-infection with 2.5 mg/kg of compound in 100 μL sterile saline solution plus 25% DMSO (V/V), vancomycin/ lysostaphin (5 mg/kg, saline solution/25% DMSO) or vehicle (saline solution/25% DMSO) as positive and negative controls respectively. Animals were closely observed during a period of 24 hours and mice that show signs of severe sepsis were humanely euthanized. Blood samples were collected by retro-orbital puncture at the indicated intervals post-infection using lithium-heparin polystyrene tubes to prevent coagulation. Spleens were harvested aseptically, weighed and homogenized in 500 μl of sterile saline solution using an IKA T10 basic disperser (IKA, Wilmington N.C.). Whole blood samples and spleen homogenates were serially diluted and plated onto LB agar plates. Bacterial counts were determined following 24 h incubation at 37° C. and expressed as CFU per milliliter for blood and CFU per gram for spleen.

Molecular Modeling of the BAS00127538-Lipid II Complex

A model of the BAS00127538-Lipid II complex was generated based on the experimental data followed by molecular dynamics (MD) simulations. Lipid II, which consists of a pentapeptide (L-Ala-D-γ-Glu-L-Lys-D-Ala-D-Ala), two cyclic sugars, N-acetylglucosamine (GlcNAc) and N-acetylmuramic acid (MurNAc), and a di-phosphate prenyl chain was generated in the program CHARMM (Brooks, B. R., et al., (2009) *Journal of Computational Chemistry* 30, 1545-1614) using the additive CHARMM force field for proteins and carbohydrates (MacKerell, A. D., et al., (1998) *Journal of Physical Chemistry B* 102, 3586-3616; Best, R. B., Zhu, X., Shim, J., Lopes, P. E. M., Mittal, J., Feig, M., and MacKerell, A. D. (2012) *Journal of Chemical Theory and Computation* 8, 3257-3273; Guvench, O., et al. (2011) *J Chem Theory Comput* 7, 3162-3180; Mallajosyula, S. S., Guvench, O., Hatcher, E., and MacKerell, A. D. (2011) *Journal of Chemical Theory and Computation* 8, 759-776). This involved creation of new topology files for MurNac, D-γ-Glu and the di-phosphate prenyl chain with missing parameters assigned by analogy. BAS00127538 was generated with the CHARMM general force field (CGENFF) (Vanommeslaeghe, K., et al. (2010) *Journal of Computational Chemistry* 31, 671-690). The starting conformation of Lipid II was obtained from the experimental NMR structure of the nisin-Lipid II complex (pdb code: 1WCO) (Hsu et al.) followed by a 2000 step steepest descent (SD) minimization and then a 200 step adopted basis Newton-Raphson (ABNR) minimization yielding a conformation with a root-mean-square (RMS) difference of 4.7 Å for all non-hydrogen atoms as compared with the experimental NMR structure.

The inhibitor-Lipid II model was built by orienting the inhibitor adjacent to Lipid II based on data from the NMR experiments. This involved manually placing one of the inhibitor benzene rings and MurNac ring in Lipid II adjacent to each other. Harmonic restraints, $k(r-r_0)^2$, were placed between the geometric centers of the above groups, where $k=50$ kcal/(mol $Å^2$), $r_0=3$ Å and r is the distance between those geometric centers. The system was then subjected to a 2000 step SD energy minimization followed by a 1 ns gas phase Langevin simulation in the presence of the restraints followed by an additional 1 ns gas phase Langevin simulation in the absence of the restraints. The resulting complex was then solvated in a 48*48*48 $Å^3$ pre-equilibrated (Jorgensen, W. L., Chandrasekhar, J., Madura, J. D., Impey, R. W., and Klein, M. L. (1983) *Journal of Chemical Physics* 79, 926-935) water box for condensed phase simulations. All water molecules within 2.8 Å of the non-hydrogen atoms of the complex are removed, and two sodium ions were added to neutralize the system, which contained 10385 atoms. While all nonbonded interactions were evaluated for gas phase simulations, nonbonded interactions were truncated at 12 Å for condensed phase simulations, with a force switch smoothing from 10 to 12 Å. Simulations were performed using periodic boundary conditions with the particle mesh Ewald summation method (Feller, S. E., Pastor, R. W., Rojnuckarin, A., Bogusz, S., and Brooks, B. R. (1996) *Journal of Physical Chemistry* 100, 17011-17020) used to treat the electrostatic interactions with a real space cutoff of 12 Å. The system was minimized for 2000 SD steps and subjected to an isobaric, isothermal (NPT) MD simulation at 300K and 1 atm. Simulations were extended for 2 ns during which the inhibitor remains in close contact with Lipid II.

Results

HNP-1 in Complex with Lipid II

The inventors have previously determined the crystal structure of chemically synthesized, wild-type HNP-1 at 1.6 Å resolution (Wei, G., de Leeuw, E., Pazgier, M., Yuan, W., Zou, G., Wang, J., Ericksen, B., Lu, W. Y., Lehrer, R. I., and Lu, W. (2009) *J Biol Chem* 284, 29180-29192). The crystal structure shows HNP-1 existing as a dimer composed of two anti-parallel monomers, each showing the "classical" defensin fold. Co-crystallization of a HNP-1/Lipid II complex was attempted. HNP-1 and soluble, 3-Lipid II were mixed in a 1:1 molar ratio. Crystals were observed in three separate crystallization conditions and all belonged to the same space group. Importantly, both crystallization conditions and space group were different from those for HNP1 alone. Crystals diffracted to 2.4 Å resolution, allowing clear identification of the HNP1 dimer. Compared to the HNP1 structure, the inventors observed additional electron density spanning the HNP1 dimer interface adjacent to residues Arg15, Ile20, Leu25.

To visualize the complex between HNP1 and Lipid II, X-ray directed docking studies using the HADDOCK program (Dominguez, C., Boelens, R., and Bonvin, A. M. (2003) *J Am Chem Soc* 125, 1731-1737) were performed. The partial complex crystal structure, together with the availability of the HNP-1 and Lipid II experimental 3D structures, made such modeling feasible. Based on the X-ray data, the amino acid side-chains of Ile20 and Leu25 of monomer A and R15, Ile20 and Leu25 of monomer B of HNP1 form the primary Lipid II binding site of HNP1 and this information was used to drive the docking (see Material and Methods). A view of the top ranking solution is shown in FIG. 1 and contact residues are listed in Table 1, FIG. 9. In the FIG. 9, common three letter abbreviations are used for amino acids. D: amino acid in D-configuration. MurNac: N-acetyl Muramic acid. The contact statistics are based on an analysis of the top 4 lid docking models.

FIG. 1 depicts (A) Crystal structure-based model of the HNP-1-Lipid II complex obtained with HADDOCK. The HNP-1 dimer is shown in surface representation. (B) Residue Isoleucine 20 of HNP-1 monomer A interacts with Lysine-3 of the Lipid II pentapeptide, whereas Leucine residue 25 of HNP-1 monomer A interacts with D-Ala at position 4. (C) Residues Arginine-15, Isoleucine 20 and Leucine-25 of HNP-1 monomer B interact with γD-Glu-2 and the phosphate/N-acetyl muramic acid moiety of Lipid II. Critical residues for the interaction are shown in cyan for HNP-1 and in magenta for Lipid II.

The interaction between HNP-1 and Lipid II involves mainly non-bonded interactions and one main chain-side chain hydrogen bond between Arg15 of HNP-1 Monomer B and D-Ala at position four of the Lipid-II pentapeptide. Ile20 of Monomer A forms non-bonded interactions with three residues of the Lipid II pentapeptide as well as the N-acetyl muramic acid (NAM) moiety. The leucines at positions 25 of both monomers interact with the NAM moiety as well. Residues Gly23 and Arg24 of the HNP-1A monomer are involved in additional interactions.

Functional Characterization and Specificity of the HNP-1-Lipid II Binding Site

Because the docking model predicts Arg15, Ile20, Gly23, Arg24 and Leu25 to form the Lipid II binding site, the present inventors expected that replacement of these residues by alanine affects Lipid II binding and bacterial killing directly. They assayed for Lipid II binding directly by Surface Plasmon Resonance using single alanine mutants of HNP-1 (Wei, G., Pazgier, M., de Leeuw, E., Rajabi, M., Li, J., Zou, G., Jung, G., Yuan, W., Lu, W. Y., Lehrer, R. I., and Lu, W. (2010) *J Biol Chem* 285, 16275-16285). As expected, replacement of the most critical residues forming the predicted Lipid II binding site by alanine (Arg15, Ile20 and Leu25) resulted in significant reduction of binding to Lipid II as compared to the wild-type HNP-1 (FIG. 2). In particular, FIG. 2 depicts: (Upper panel) Binding of HNP-1 and HNP-1 single alanine mutants on immobilized Lipid II as determined by SPR at room temperature. Representative sensorgrams of one out of two separate experiments of HNP-1 and analogues at 10 μM using a sensorchip with 40 RUs of soluble, 3-Lipid II. (Lower panel) Quantification of binding of HNP-1 mutants compared to binding of wild-type HNP-1, set as 100%.

In contrast, replacement of Arg5, Ile10 or Gly23 by alanine did not affect binding to Lipid II, indicating that these residues are not important for Lipid II binding. The HNP-1 R24A mutant maintained significant binding to Lipid II, suggesting that this residue contributes, but does not make a critical contribution to Lipid II binding.

Figure 12:
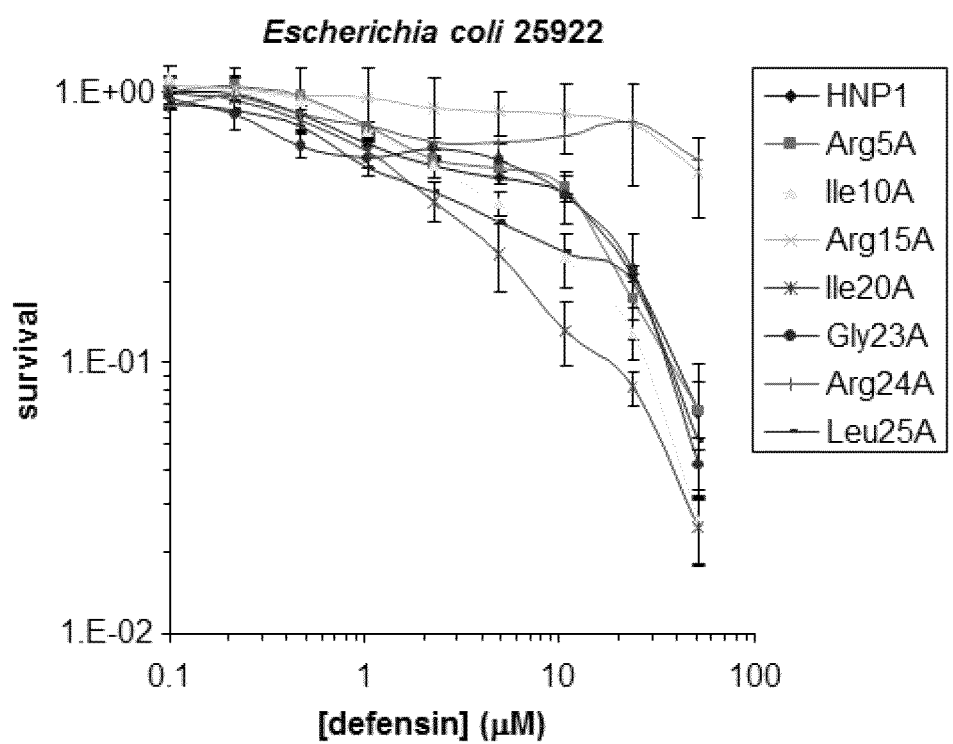
FIG. 12 depicts survival curves that indicate killing of *E. coli* by HNP-1 Lipid II single alanine mutants.

The inventors have previously reported on the antibacterial activity of HNP1 and all of its structurally uncompromised single alanine mutants against *S. aureus* (Wei, G., Pazgier, M., de Leeuw, E., Rajabi, M., Li, J., Zou, G., Jung, G., Yuan, W., Lu, W. Y., Lehrer, R. I., and Lu, W. *J Biol Chem* 285, 16275-16285). It was shown that replacement of the Trp26 by alanine significantly reduced its activity, likely due to disrupting a functional HNP-1 dimer (Wei, et al., *J Biol Chem* 284, 29180-29192, Wei, et al., W. *J Biol Chem* 285, 16275-16285). In addition to Trp26, the inventors observed that killing of *S. aureus* by HNP-1 was also severely compromised by single mutations of Arg15, Ile20 or Leu25 into an alanine (Wei, et al, *J Biol Chem* 285, 16275-16285), in agreement with that present model that predicts that these residues map to the Lipid II binding site. If these residues are indeed important for Lipid II binding, one would expect that replacement by alanine will not affect killing of Gram-negative bacteria. Indeed, when tested against *E. coli*, these single alanine mutants showed bactericidal activity comparable to the wild-type peptide, with exception of the Arg15 mutant (FIG. 12). In particular, FIG. 12 depicts killing of *E. coli* by HNP-1 Lipid II single alanine mutants. Survival curves of *E. coli* ATCC 25922 exposed to HNP-1 or HNP-1 single alanine mutants at concentrations varying two-fold from 0.3 to 50 mM. Bacteria were exposed to defensin peptides for 120 min. Each curve is the mean of two separate experiments (±S.D.). Points scored as zero survival could not be plotted.

Figure 3:
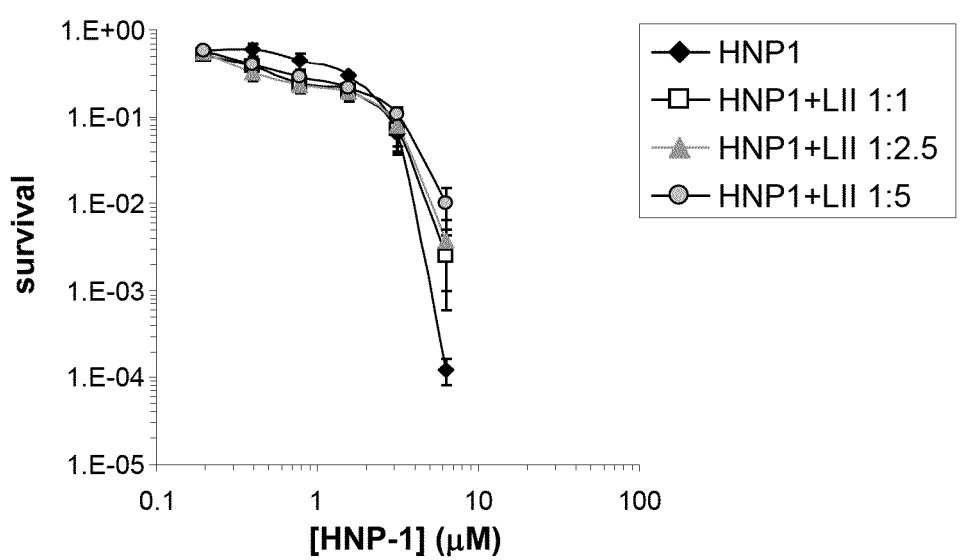
FIG. 3 shows that lipid II antagonizes the antibacterial activity of HNP-1. Survival curves of *S. aureus* ATCC 29213 exposed to HNP1 (at concentrations varying two-fold from 50 to 1.25 μM).

Next, the inventors examined whether the antibacterial activity of HNP-1 could be antagonized by soluble Lipid II as a measure for functional interaction. HNP-1 (50 µM) was pre-incubated with 3-Lipid II at varying molar ratios and killing of S. aureus was determined using the vCC protocol (Erickson et al.) (FIG. 3). The bactericidal activity of the HNP-1 peptide appeared reduced by one order of magnitude by the presence of Lipid II in a 1:1 molar ratio. The activity was only slightly reduced further by increasing the amount of Lipid II. FIG. 3 shows that lipid II antagonizes the antibacterial activity of HNP-1. Survival curves of S. aureus ATCC 29213 exposed to HNP1 (at concentrations varying two-fold from 50 to 1.25 µM). Defensin peptide was pre-incubated with 3-Lipid II at varying molar ratios for 30 min prior to addition of bacteria. Bacteria were subsequently exposed to HNP-1 for 30 min. Each curve is the mean of two separate experiments (±S.D.). Points scored as zero survival could not be plotted.

The model suggests the HNP-1-Lipid II binding involves interactions between HNP-1 and the pentapeptide chain of Lipid II, including the D-Ala residue at position four. The D-Ala-D-Ala motif in the pentapeptide is the predominant binding site for vancomycin, a drug of "last resort" for many multi-drug resistant Gram-positive infections. To examine if the interaction of HNP-1 with Lipid II overlaps with the vancomycin binding site, antagonization assays were performed. Diacetyl-Lys-D-Ala-D-Ala (D-Ala) was used as agonist and the non-specific peptide diacetyl-Lys-D-ala-D-Lac (D-Lac) as a control. Both vancomycin and HNP-1 were pre-incubated at a 1:200 molar ratio with both compounds for 30 min, similar to experiments with soluble Lipid II (FIG. 3). Subsequently, the inventors determined any antagonizing effects on the killing of S. aureus (FIG. 4). FIG. 4 shows that the Lipid II pentapeptide does not antagonize the antibacterial activity of HNP-1. In particular, survival curves of S. aureus ATCC 29213 exposed to HNP1 (upper panel) at concentrations varying two-fold from 50 to 1.25 µM or to vancomycin (lower panel) at concentrations varying two-fold from 2 to 0.0125 µM. HNP-1 and vancomycin were pre-incubated with D-ala or D-lac at a 1:200 molar ratio for 30 min prior to addition of bacteria. Bacteria were subsequently exposed to HNP-1 or vancomycin for 30 min. Each curve is the mean of two separate experiments (±S.D.). Points scored as zero survival could not be plotted.

Vancomycin killed S. aureus very effectively and bacterial growth was visible only at the two lowest concentrations used (1.9 and 3.9 µg/ml). At higher concentrations, bacterial growth did not recover and as a result no data points could be plotted. Pre-incubation of vancomycin with the agonist D-Ala specifically inhibited the killing of S. aureus, whereas the bactericidal activity was not altered by the presence of the control peptide D-Lac. Importantly, HNP-1 was not competitively inhibited by either compound, suggesting that the primary mode of interaction of HNP-1 to Lipid II differs from that of vancomycin.

In conclusion, structural, functional and in silico analyses map the Lipid II binding of HNP-1 to hydrophobic residues at its C-terminus, involving predominantly non-bonded interactions with the interface of the MurNac moiety and pentapeptide of Lipid II. The mode of interaction of HNP-1 to Lipid II differs from that of vancomycin, possibly suggesting that interactions between HNP-1 and the Lipid II pentapeptide are functionally less relevant.

Identification and Functional Characterization of Defensin Mimetics

Given the antimicrobial activity of HNP-1, it was reasoned that compounds that mimic the interaction between HNP-1 and Lipid II could have potential antibiotic use. To identify low molecular weight compounds that can mimic the spatial orientation of the side chains in the HNP-1 dimer that bind Lipid II, a search of commercially available drug-like compounds was undertaken. 3D TAT pharmacophore fingerprints were used to describe the physical properties and spatial relationships of residues Ile20 and Leu25 of monomer A, and Arg15, Ile20 and Leu25 of monomer B in the HNP-1 dimer. This information was then used in a pharmacophore search to identify compounds with the desired features. After the first round of biological testing, five active compounds were identified and two types of similarity searching were conducted. The first method is based on chemical similarity and may potentially identify compounds with improved activity as well as produce data allowing for a structure-activity relationship for the compounds to be developed that may be of utility of subsequent ligand design. Searching was also performed based on physiochemical properties that may lead to the identification of novel chemical structures that represent new lead compounds In total, 75 compounds from the two rounds of similarity searches were selected. All compounds were tested for antibacterial activity, binding to Lipid II by Surface Plasmon Resonance and for cytotoxicity against two human cell lines. Out of 75 compounds, 28 (37.6%) were identified that showed specific killing against S. aureus over E. coli. Seventeen compounds (22.6%) showed significant binding to Lipid II. 6.6% of all compounds were equally active against S. aureus and E. coli (5/275) and 46% (42/75) showed no activity (42/75). Results for all compounds are summarized in FIG. 14.

Characterization of Lead Defensin Mimetics

Figure 14:
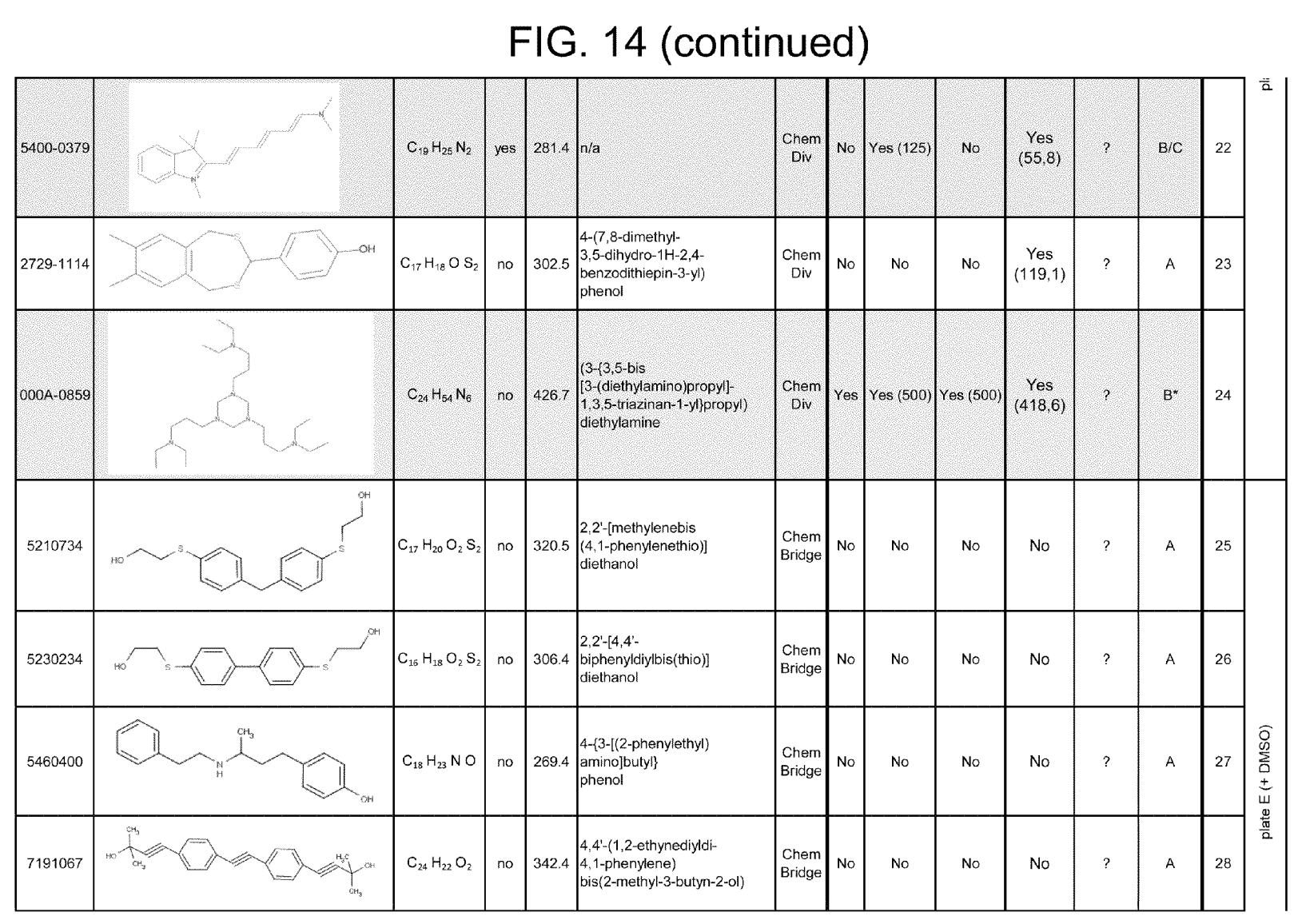

Based on the assays described in FIG. 14, the low-molecular weight compounds selected as potential defensin mimetics were classified based on chemical structures, Lipid II binding, cytotoxicity and preferential Gram-positive killing (Table 2, FIG. 10).

Figure 5:
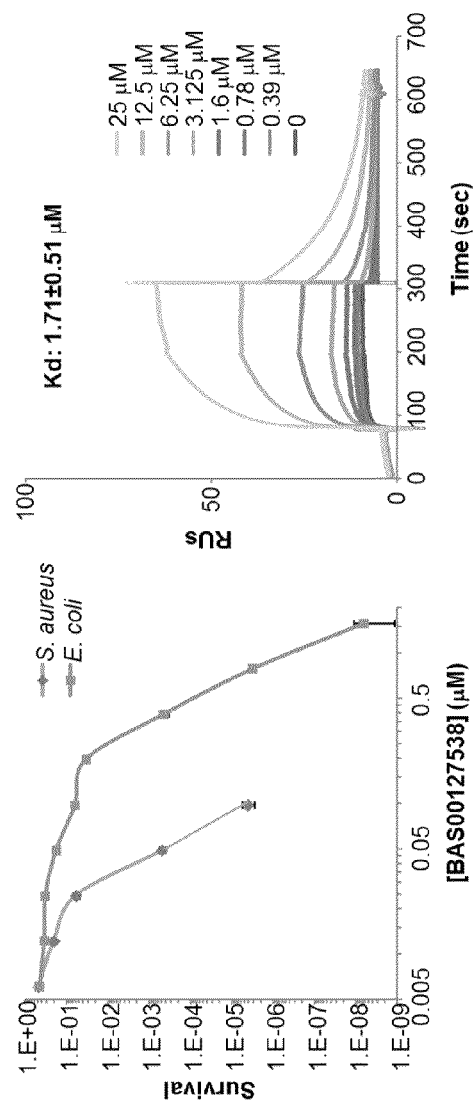
FIG. 5 depicts the chemical structure for one of the present compounds, BAS00127538 (left panel); bacterial killing (middle panel) and Lipid II binding (right panel) of defensin mimetic BAS00127538. Mimetic compound was 100% bactericidal at 0.244 μM against *S. aureus* and 7.8 μM against *E. coli*. Points of zero survival could not be plotted. (right panel) Representative sensorgrams of one out of three experiments of BAS00127538 binding to immobilized 3-Lipid II.

FIG. 5 shows the results for lead compound BAS00127538 as an example of the present molecules. This compound most strongly bound to Lipid II as measured by SPR and potently killed S. aureus bacteria. In particular, FIG. 5 depicts the chemical structure for one of the present compounds, BAS00127538 (left panel); bacterial killing (middle panel) and Lipid II binding (right panel) of defensin mimetic BAS00127538. Mimetic compound was 100% bactericidal at 0.244 µM against S. aureus and 7.8 µM against E. coli. Points of zero survival could not be plotted. (right panel) Representative sensorgrams of one out of three experiments of BAS00127538 binding to immobilized 3-Lipid II.

To confirm the antibacterial killing assays, Minimal Inhibitory Concentrations (MICs, µg/ml) were determined for lead compounds against clinically relevant bacterial strains (Table 3, FIG. 11). In particular, Table 3 shows broth microdilution susceptibility testing for lead defensing mimetics and comparators. Experiments were carried out according to CLSI standards (CLSI. (2009) *Methods for Dilution Antimicrobial Susceptibility Tests for Bacteria That Grow Aerobically; Approved Standard—Eighth Edition*.) by Micromyx, LLC (Kalamazoo, Mich.). MIC values for comparators (Ciprofloxin and Linezolid) were within QC range (Humphrey et al.). In agreement with the killing assays, lead defensin mimetics tested were potently active against Gram-positive isolates, and generally no activity was apparent against Gram-negative isolates, with the exception of BAS00127538, which had MICs of 4 µg/ml when tested against *E. coli*. There was no significant difference for any compound when evaluated against clinically relevant strains (e.g. MRSA, VRE, PRSP).

Figure 6:
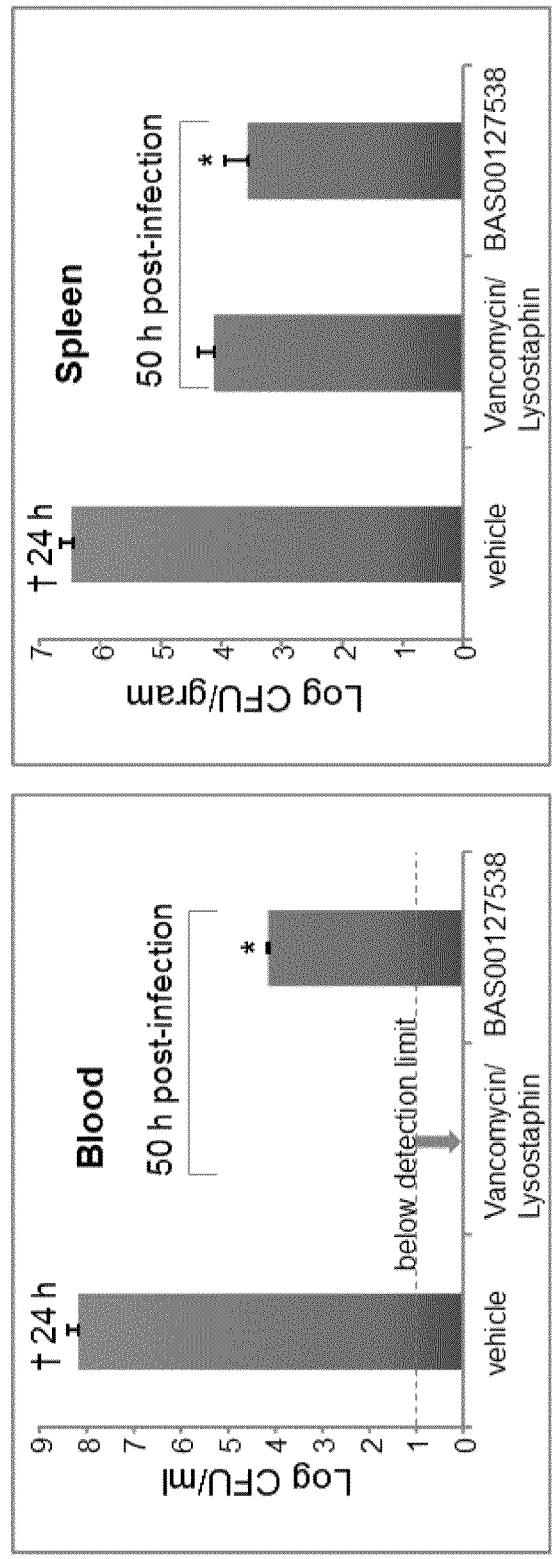
FIG. 6 depicts the efficacy of BAS00127538 in vivo. Blood samples were collected from vehicle-treated animals at 20 h or at 50 h post-infection from vancomycin and BAS00127538-treated animals. * One animal treated with compound did not survive beyond 28 h.

Next, a murine model for sepsis was established to evaluate the efficacy of the lead defensin mimetics as antibiotic agents in vivo. Preliminary experiments indicated that the lead compounds listed in Table 2 (FIG. 10) were effective at 5 mg/kg in clearing non-lethal doses of *S. aureus* 29213 bacteria when administered intraperitoneally (not shown). Lead compound BAS00127538 proved most efficacious and was selected for further experimentation. Mice (n=5) were inoculated intraperitoneally with *S. aureus* 29213 and treated 1 h and 4 h post-infection with compound BAS00127538 at 2.5 mg/kg intraperitoneally Animals were monitored for survival and blood and spleen samples were collected. Bacterial counts were determined and compared to control treatment with vancomycin/lysostaphin as measures of efficacy (FIG. 6). FIG. 6 depicts the efficacy of BAS00127538 in vivo. Blood samples were collected from vehicle-treated animals at 20 h or at 50 h post-infection from vancomycin and BAS00127538-treated animals. * One animal treated with compound did not survive beyond 28 h Animals treated with vehicle did not survive after 24 h. Animals treated with vancomycin/lysostaphin survived the length of the experiment and bacterial counts in blood and spleen were in accordance with published data (Reyes, N., Skinner, R., Benton, B. M., Krause, K. M., Shelton, J., Obedencio, G. P., and Hegde, S. S. (2006) *The Journal of antimicrobial chemotherapy* 58, 462-465). Treatment with BAS00127538 resulted in survival of 4 out of five animals and significantly reduced bacterial counts in spleen and blood, indicative of in vivo antibiotic efficacy.

Interaction of Lead Defensin Mimetic BAS00127538 with Lipid II

To confirm the binding of defensins mimetic BAS00127538 to Lipid II the inventors observed by SPR, their interaction was studied directly by NMR (FIG. 7). Specifically, the inventors used 1D proton NMR spectra to determine if any chemical shift changes occur when the compound was added to 3-Lipid II. BAS00127538 was found to interact and was analyzed further by 2D TOCSY, NOESY, and natural abundance $^{13}$C HSQC analyses (FIG. 7, upper panel). This Figure depicts an analysis of 2D TOCSY spectra collected at 800 MHz of the aromatic region of compound BAS00127538 alone (black) overlaid with spectra of compound bound to Lipid II (red). Large chemical shifts were observed on the face of this compound that contains two aromatic rings (FIG. 5). No chemical shifts were observed for the methyl groups on the opposite side of the molecule (not shown). Analysis of 3-Lipid II NMR spectra with and without compound allowed the interaction to be pinpointed to the N-Acetylmuramic acid moiety (MurNAc) of lipid II (FIG. 7, lower panel). The lower panel shows 2D natural abunance $^{13}$C HSQC spectrum illustrating the interaction between Lipid II and the compound BAS00127538. BAS00127538 alone (black) is overlaid with a spectrum of compound bound to Lipid II (red). Spectra were collected on a Bruker 800 MHz Avance NMR spectrometer at 25 degrees. Chemical shift changes for Lipid II upon BAS00127538 compound binding suggest that the interaction is occurring at or near the MurNAc moiety of Lipid II. No chemical shifts for the pentapeptide Alanine residues could be observed.

Figure 8:
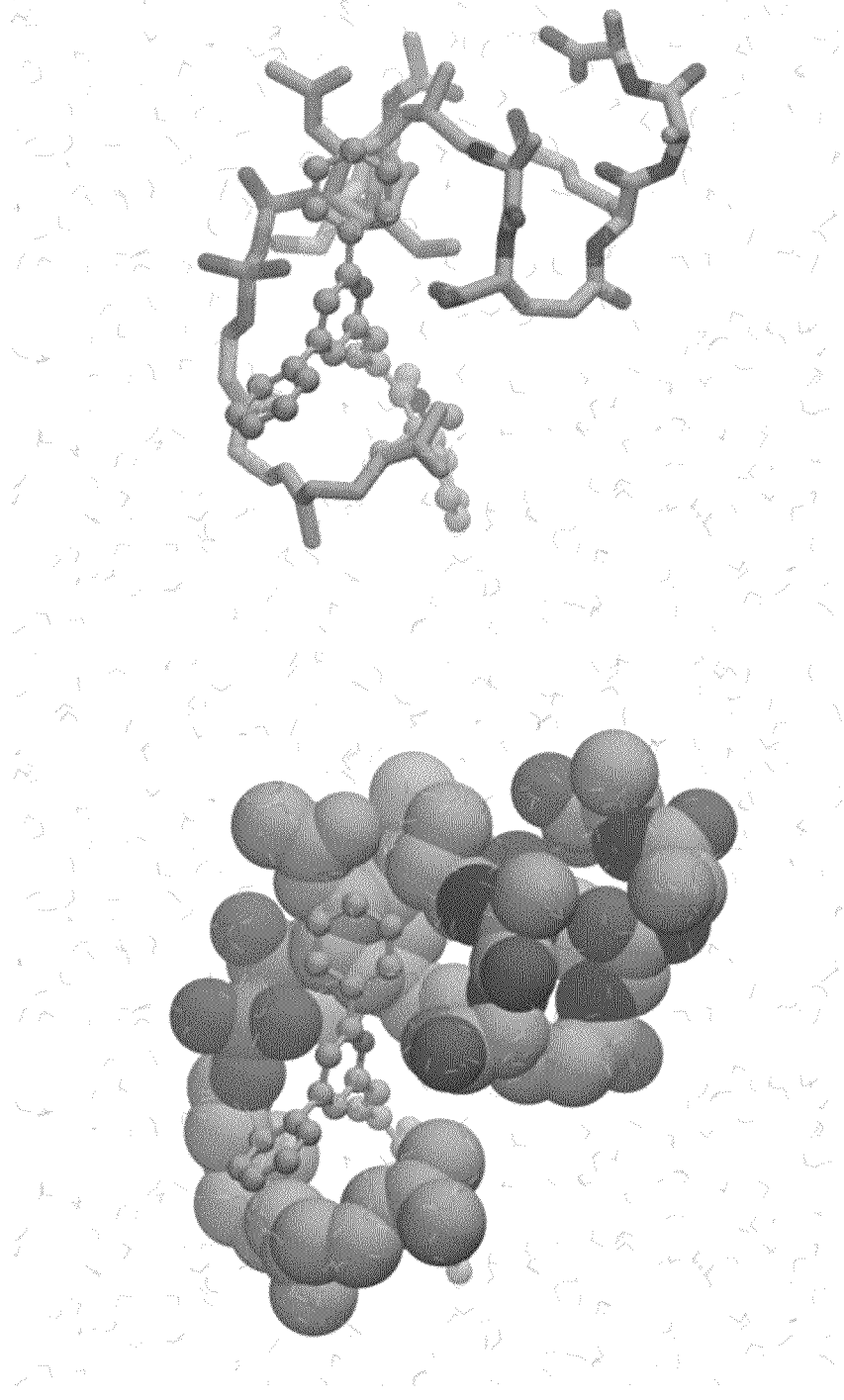
FIG. 8 depicts a model of the BAS00127538-lipid II complex obtained with CADD in conjunction with the NMR data. Upper panel includes BAS00127538 shown in CPK atom-colored representation, Lipid II in a licorice, atom-colored representation, with the exception of the N-MurNac moeity, which is green, and water molecules included in the simulation are shown in stick format. Lower panel is the same as upper panel except Lipid II is shown in van der Waals representation. Images created with VMD (Humphrey, W., Dalke, A., and Schulten, K. (1996) *J Mol Graph* 14, 33-38, 27-38).

Based on the NMR data, MD simulations were used to model the BAS00127538-3-Lipid II complex. This involved initially restraining each aromatic ring to be adjacent to MurNAc followed by explicit solvent MD simulations in which the restraint was removed following an equilibration period. The resulting model which was stable in the explicit MD simulation is shown in FIG. 8. One aromatic ring of BAS00127538 lies over the MurNAc moiety (green) of Lipid II (bond, atom color except for MurNAc in green) consistent with the NMR data with the positively charged pyran ring of the inhibitor between the phosphate and acid moieties of Lipid II. In addition, the isoprenyl tail of lipid II forms a hydrophobic pocket that interacts with the second aromatic ring and the linker to indolylene ring. FIG. 8 depicts a model of the BAS00127538-lipid II complex obtained with CADD in conjunction with the NMR data. The upper panel includes BAS00127538 shown in CPK atom-colored representation, Lipid II in a licorice, atom-colored representation, with the exception of the N-MurNac moiety, which is green, and water molecules included in the simulation are shown in stick format. The lower panel is the same as upper panel except Lipid II is shown in van der Waals representation. Images created with VMD (Humphrey, W., Dalke, A., and Schulten, K. (1996) *J Mol Graph* 14, 33-38, 27-38).

Discussion

Here, the inventors have discovered the unique interaction of HNP-1 with Lipid II. This information was used to identify low-molecular weight drug-like molecules that act as Defensin mimics using computer-aided drug design (CADD). Subsequent experimental characterization of these compounds showed several which show preferential activity against Gram-positive organisms while being non-toxic to host cells at comparable concentrations. One promising compound was further characterized showing in vivo protection of sepsis and a unique interaction with the MurNac moiety of Lipid II. To the inventors' knowledge, this is the first time a low-molecular weight compound that targets Lipid II has been identified.

The view on how antimicrobial peptides kill micro-organisms has been nuanced in the last few years. The broad traditional view of killing comprises an initial phase of electrostatic attraction of mostly cationic peptides to negatively charged molecules on the surface of micro-organisms (Brogden, K. A. (2005) *Nat Rev Microbiol* 3, 238-250). Following initial attraction, antimicrobial peptides disrupt membrane integrity, causing leakage of cellular content and cell death. In fact, synthetic compounds that cause membrane disruption are effective antimicrobials and have been extensively studied (Lienkamp, K., and Tew, G. N. (2009) *Chemistry* 15, 11784-11800, Palermo, E. F., and Kuroda, K. (2010) *Applied microbiology and biotechnology* 87, 1605-1615). Their killing mechanism depends on distribution of positive charge and hydrophobicity, is largely species-independent and does not involve a specific bacterial target molecule.

A functional interaction between defensins and Lipid II has only recently been determined as a novel way by which these versatile peptides act against bacteria (de Leeuw, E., Li, C., Zeng, P., Diepeveen-de Buin, M., Lu, W. Y., Breukink, E., and Lu, W. (2010) *FEBS Lett* 584, 1543-1548, Schneider et al.). In their landmark report, Schneider et al reported on the fungal defensin plectasin binding to Lipid II. The study identified interactions between plectasin and the solvent-exposed pyrophosphate region of Lipid II (Schneider et al.). These interactions involved residues Phe2, Glu3, Cys4 and C27 as well as the N-terminus and His 18 side-chain of this defensin. C-terminal hydrophobic residues were identified as Ile20 and Leu25 of HNP-1 to be mainly involved in Lipid II binding.

Using single alanine scanning analysis, the inventors previously identified residues in HNP-1 important for *S. aureus* killing, anthrax lethal factor neutralization and binding to GP120 (Wei, et al., *J Biol Chem* 285, 16275-16285). It was shown that for HNP-1 replacement of the Trp26 residue by alanine critically diminished its function, likely due to disruption of dimer formation (Wei, et al., *J Biol Chem* 285, 16275-16285). The findings further support the importance of the C-terminal region of defensins for their functionality.

Importantly, the binding sites of plectasin and HNP-1 to Lipid II did not overlap with the vancomycin binding site on Lipid II. The mechanism of resistance to vancomycin involves specific modifications of the amino acid composition of the pentapeptide in the Lipid II molecule (Sujatha, S., and Praharaj, I. (2012) *Interdiscip Perspect Infect Dis* 2012, 781679). Such modifications often occur rapidly within bacterial populations, likely due to the high degree of flexibility and variability of amino acid synthesis and incorporation (Sujatha, et al.). However, HNP-1 and defensin mimetic BAS00127538 target the aminosugar moiety of the Lipid II molecule, thus making cross-resistance with vancomycin unlikely. In addition to modification of the pentapeptide, modifications in the aminosugar residues in Lipid II that make up the peptidoglycan subunit can cause resistance also for many Gram-positive pathogens (Vollmer, W. (2008) *FEMS microbiology reviews* 32, 287-306). Such modifications often involve chemical modifications such as acetylation or deacetylation. Since resistance has developed against all antibiotics currently in clinical use, resistance against compounds that may be derived from BAS00127538 is likely (Breukink, et al., Vollmer). Nevertheless, this study may provide insight for future development, design and synthesis of efficient, defensin-derived compounds specifically targeting Lipid II as promising therapeutic leads.

Example 4

FIG. 13 depicts evidence of efficacy (MIC's) of certain compounds according to non-limiting embodiments of the present invention, using ciprofloxacin as comparator, against bacteria including *Bacillus anthracis.*

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of treating an infection in a mammal, comprising administering to the mammal a therapeutically effective amount of at least one molecule selected from the group consisting of Compound D, BAS00127538 (Asinex, 3-PC-2)

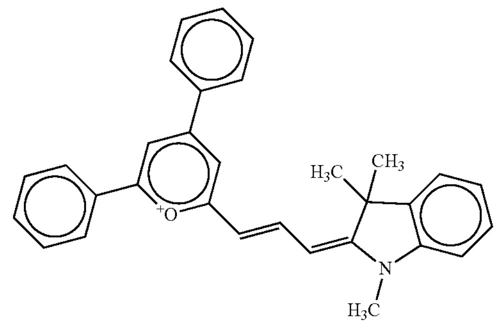

and, derivatives, and analogs thereof, wherein said infection is caused by microorganisms comprising one or more gram-positive bacteria selected from the group consisting of *Staphylococcus, Streptococcus*, and *Enterococcus.*

2. The method of claim 1, wherein said gram-positive bacteria comprises one or more bacteria selected from the group consisting of *Staphylococcus aureus, Streptococcus pyogenes, Streptococcus agalactiae, Streptococcus anginosus* group, *Enterococcus faecalis, Enterococcus faecium*, and *Bacillus Anthracis.*

3. The method of claim 1, wherein said infection is sepsis.

4. A method of killing a bacterial population in a mammal comprising administering to a mammal infected with at least one bacterial population a therapeutically effective amount for killing the bacterial population, of at least one molecule selected from the group consisting of:

Compound D, BAS00127538 (Asinex, 3-PC-2)

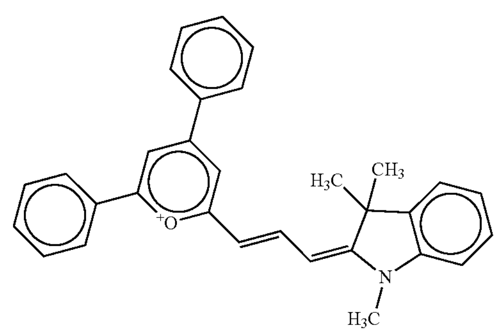

and, derivatives, and analogs thereof, wherein said infection is caused by microorganisms comprising one or more gram-positive bacteria selected from the group consisting of *Staphylococcus, Streptococcus*, and *Enterococcus.*

5. The method of claim 4, wherein the bacterial population comprises at least one bacteria selected from the group consisting of *Staphylococcus aureus, Streptococcus pyogenes, Streptococcus agalactiae, Streptococcus anginosus* group, *Enterococcus faecalis, Enterococcus faecium*, and *Bacillus Anthracis.*

6. The method of claim 4, wherein the at least one compound is administered to the mammal as part of a composition.

* * * * *